United States Patent

Kanner et al.

[19]

[11] Patent Number: 6,105,828
[45] Date of Patent: Aug. 22, 2000

[54] NON-BUBBLE FORMING DROPPER TIP

[75] Inventors: Rowland W. Kanner, Guntersville; Paul Wesley Lombard, Huntsville, both of Ala.; Joseph Murray Ault, Jr., Blairestown, N.J.

[73] Assignees: Atrion Medical Products, Inc., Arab, Ala.; Baush and Lomb Pharmaceuticals, Inc., Tampa, Fla.

[21] Appl. No.: 09/064,331

[22] Filed: Apr. 22, 1998

[51] Int. Cl.$^7$ .................................................. B65D 37/00
[52] U.S. Cl. ........................................... 222/212; 222/420
[58] Field of Search .................................. 222/212, 420, 222/421, 422

[56] References Cited

U.S. PATENT DOCUMENTS

| 4,568,004 | 2/1986 | Goncalves | 222/422 |
|---|---|---|---|
| 4,938,389 | 7/1990 | Rossi et al. | 222/420 |
| 5,125,544 | 6/1992 | Millner et al. | 222/420 |
| 5,154,702 | 10/1992 | Foyil | 222/420 |
| 5,769,278 | 6/1998 | Kummer et al. | 222/422 |
| 5,906,300 | 5/1999 | Horie | 222/420 |

FOREIGN PATENT DOCUMENTS

| 501779 | 3/1951 | Belgium | 222/420 |
|---|---|---|---|
| 2581975 | 11/1986 | France | 222/421 |

OTHER PUBLICATIONS

Adhesives Age, May 15, 1989, pp. 7–9.
Machinery's Handbook, "Surface Texture", Edition 24, pp. 671–674.
American Society for Testing and Materials, "Standard Test Method for Wetting Tension of Polyethylene and Polypropylene Films", pp. 1–3.
The Loctite Design Guide for Bonding Plastics, vol. 2, pp. 74, 79–81.

*Primary Examiner*—Joseph A. Kaufman
*Attorney, Agent, or Firm*—Trexler, Bushnell, Giangiorgi & Blackstone, Ltd.

[57] ABSTRACT

A dropper tip which is adapted to be connected to a container for dispensing fluid, such as medications and like, from the container includes a body having first and second opposite ends and an inner wall defining a conduit therethrough. The inner wall smoothly diverges and gradually increases in inner diameter from the first end to the second end such that air bubbles are prevented from being permanently trapped along the inner wall. The inner wall is highly polished and may be made of olefinic material, silicone rubber material, or fluorocarbon, including, but not limited to, polytetrafluoroethylene (PTFE), carbon tetrafluoroethylene (CTFE), fluoroethylene propylene (FEP) or the like, to resist fluid wetting, facilitate fluid detachment therefrom and to reduce fluid film thickness therealong. The surface of the inner wall is smoothed to minimize surface roughness. A tubular portion having a flat end surface is provided at the first end of the body to promote limited momentary attachment of fluid thereto when fluid is being dispensed from the dropper tip. A sharp perimeter edge is provided by the flat end surface to provide an instant transition to discourage fluid wetting and migration beyond the designated perimeter of the flat end surface. A novel cap is provided for sealing the dropper tip from contaminants.

41 Claims, 22 Drawing Sheets

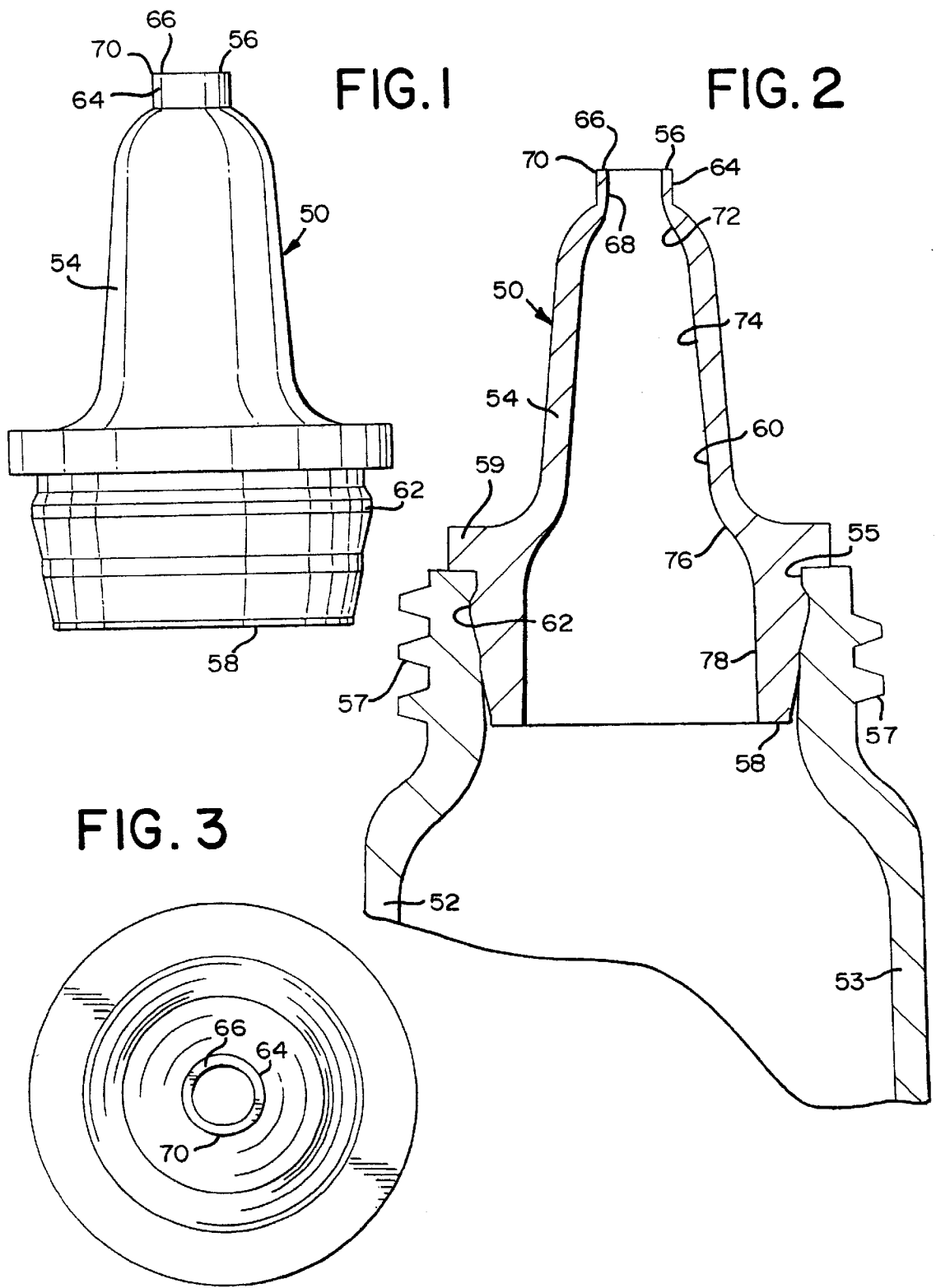

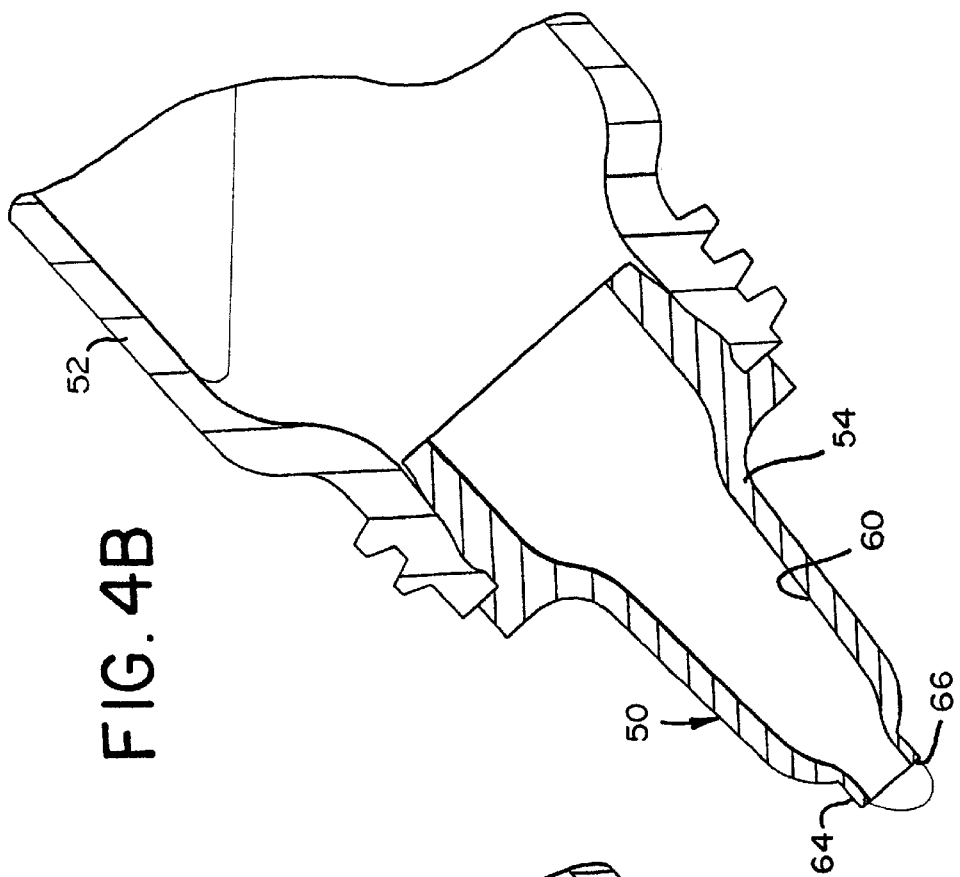
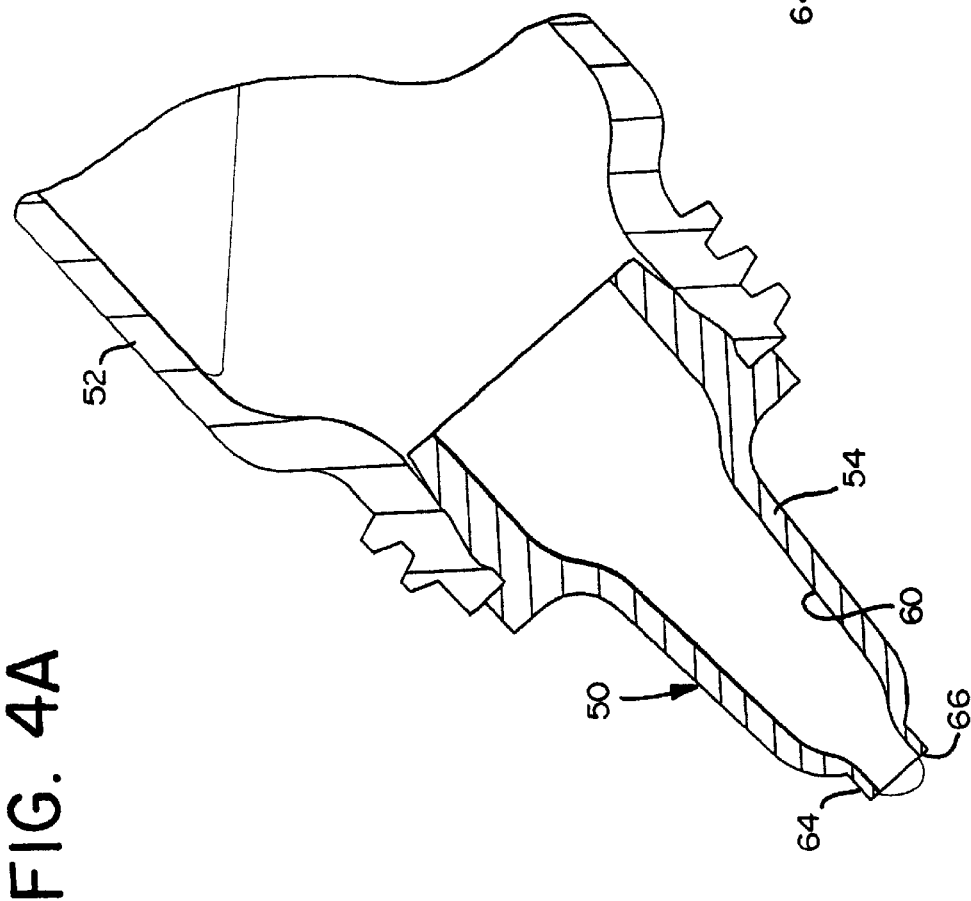

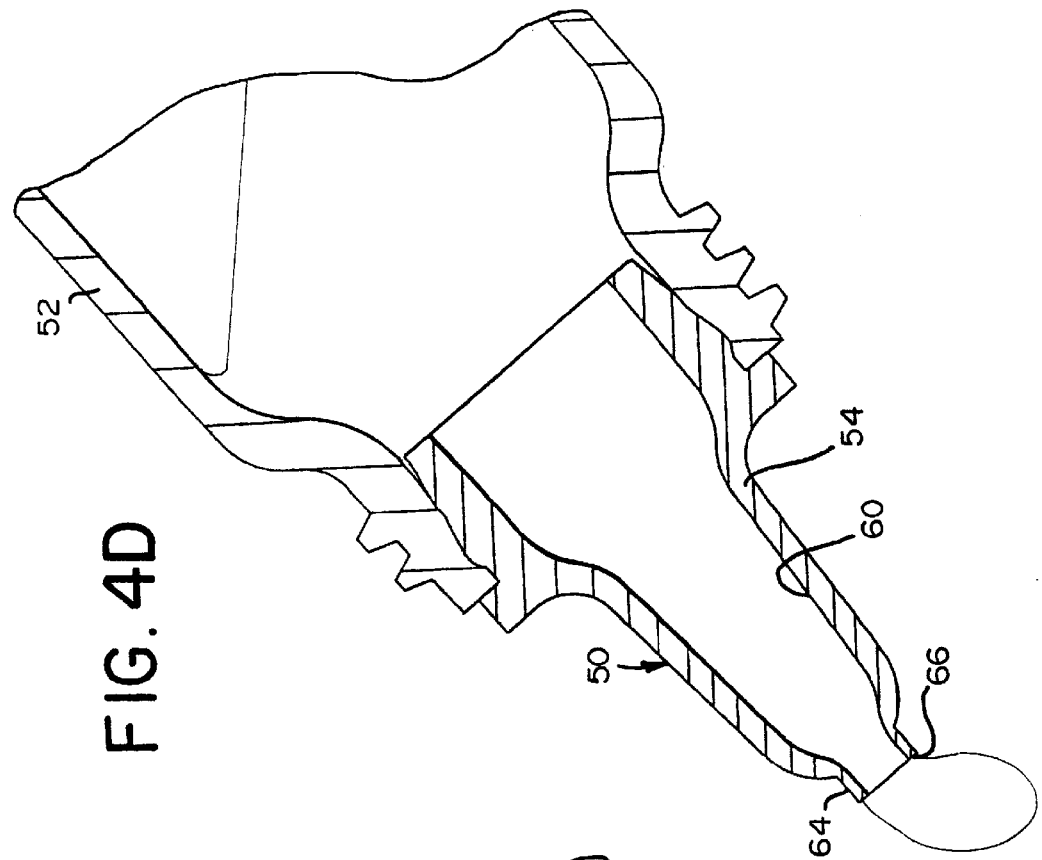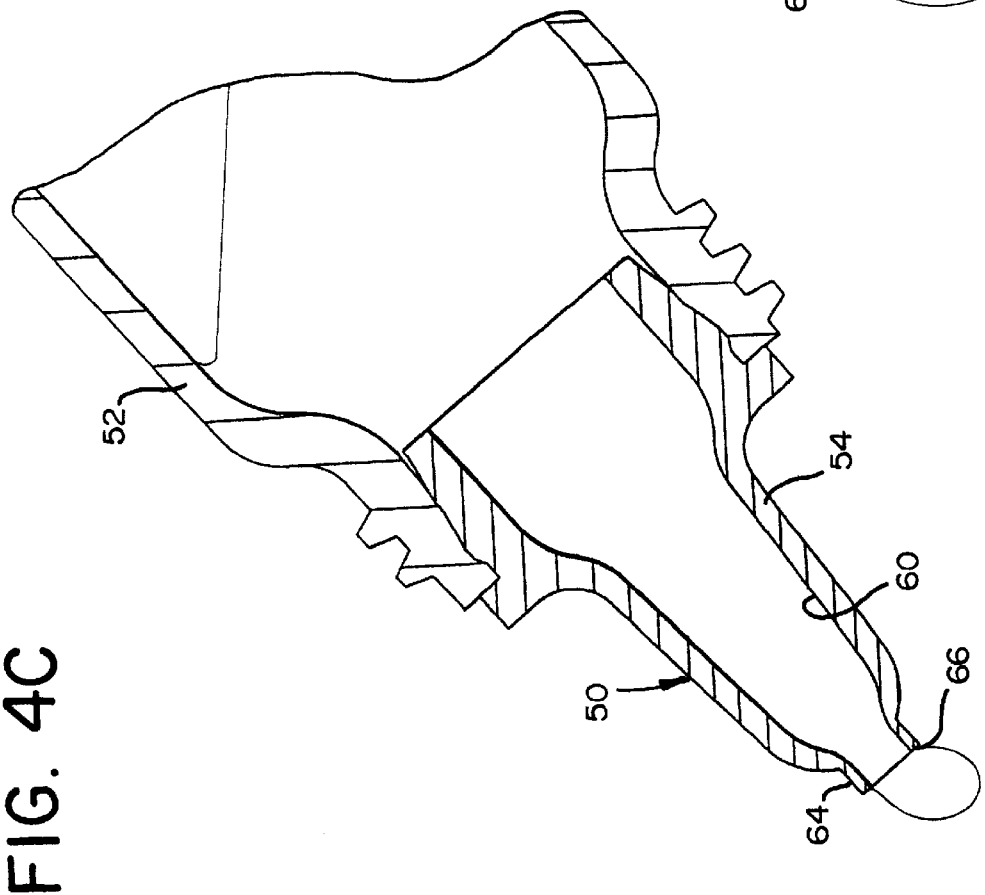

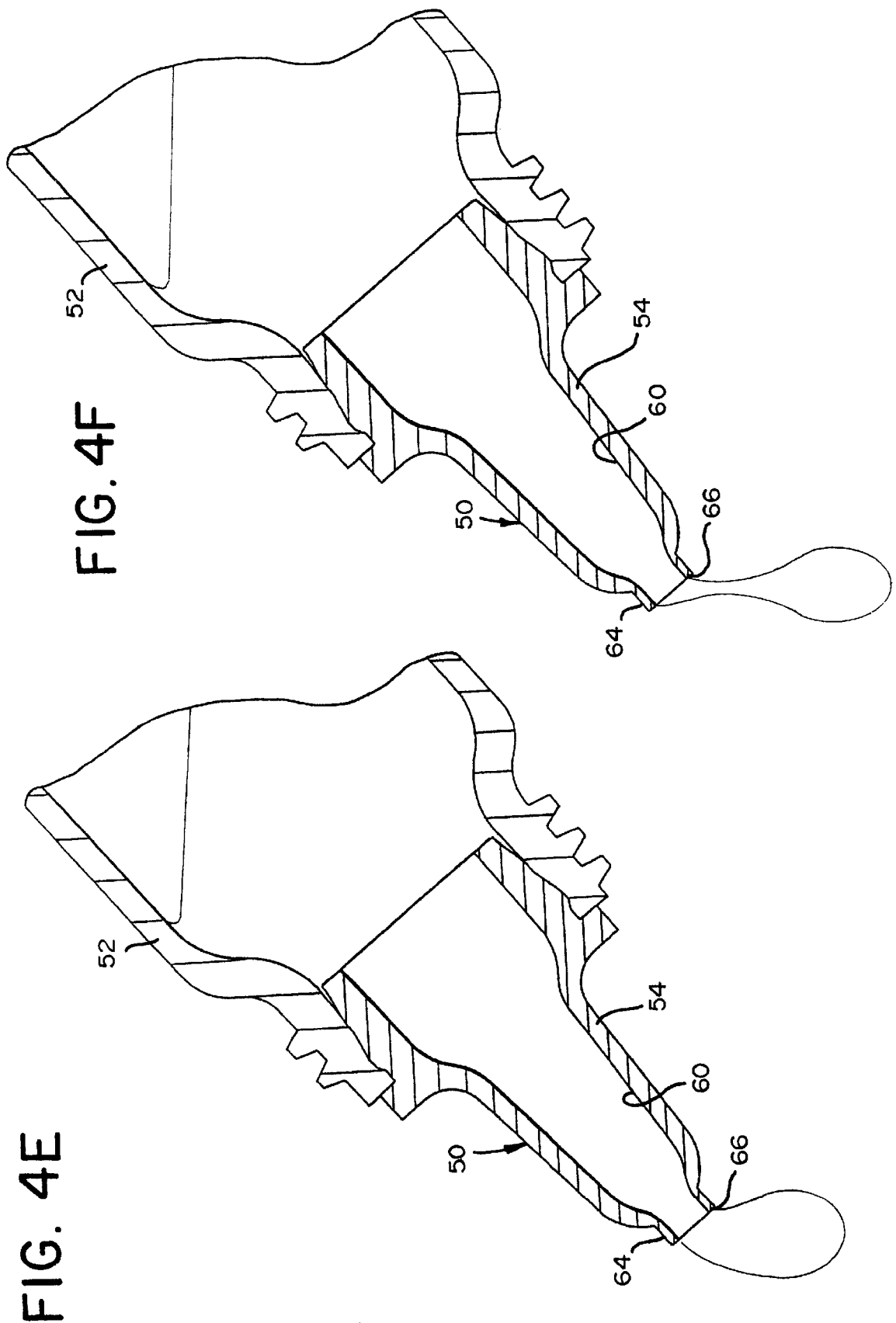

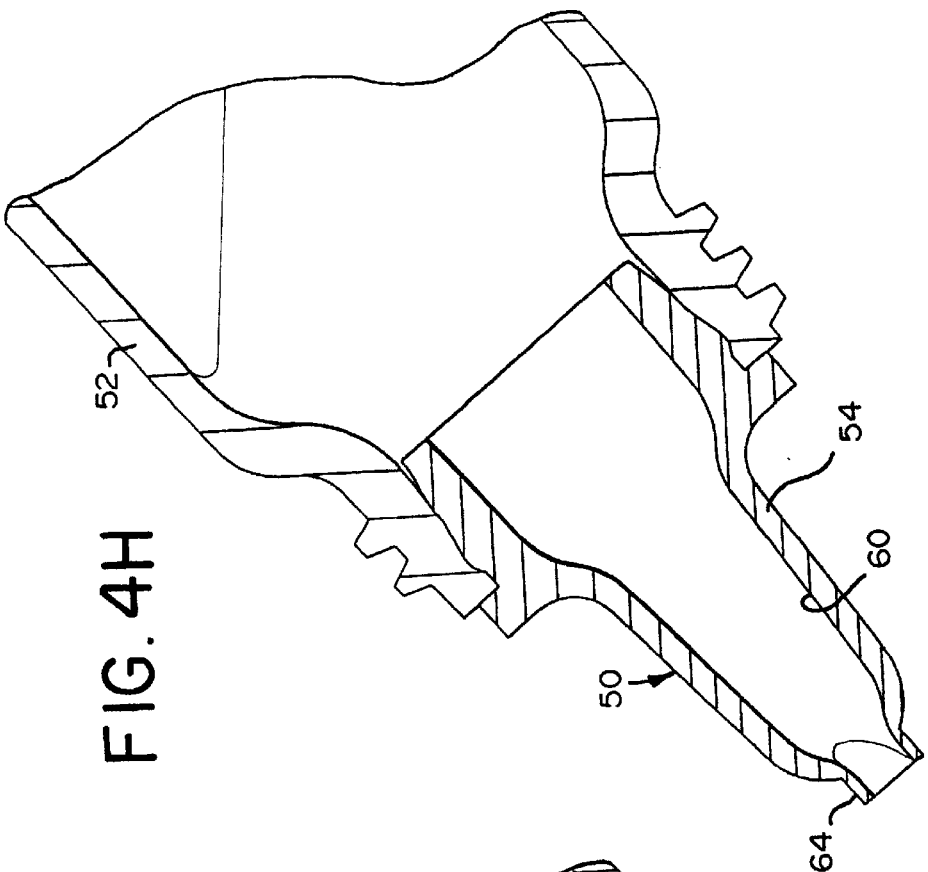
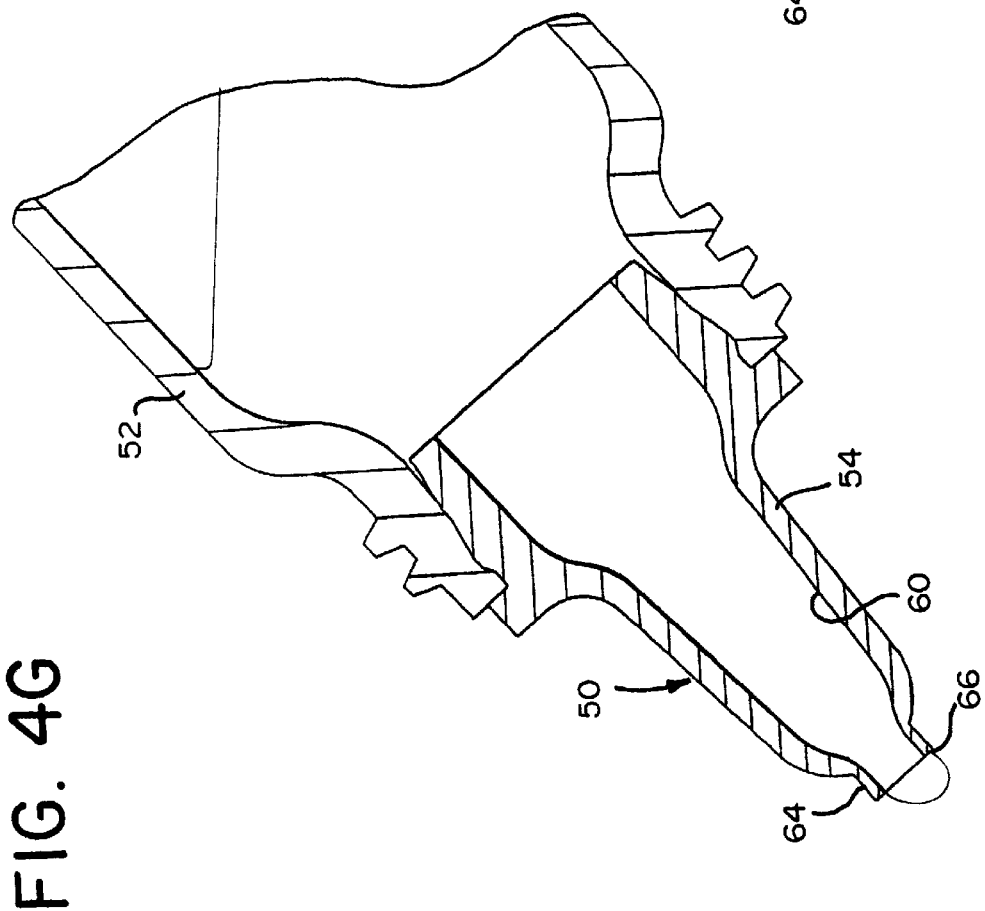

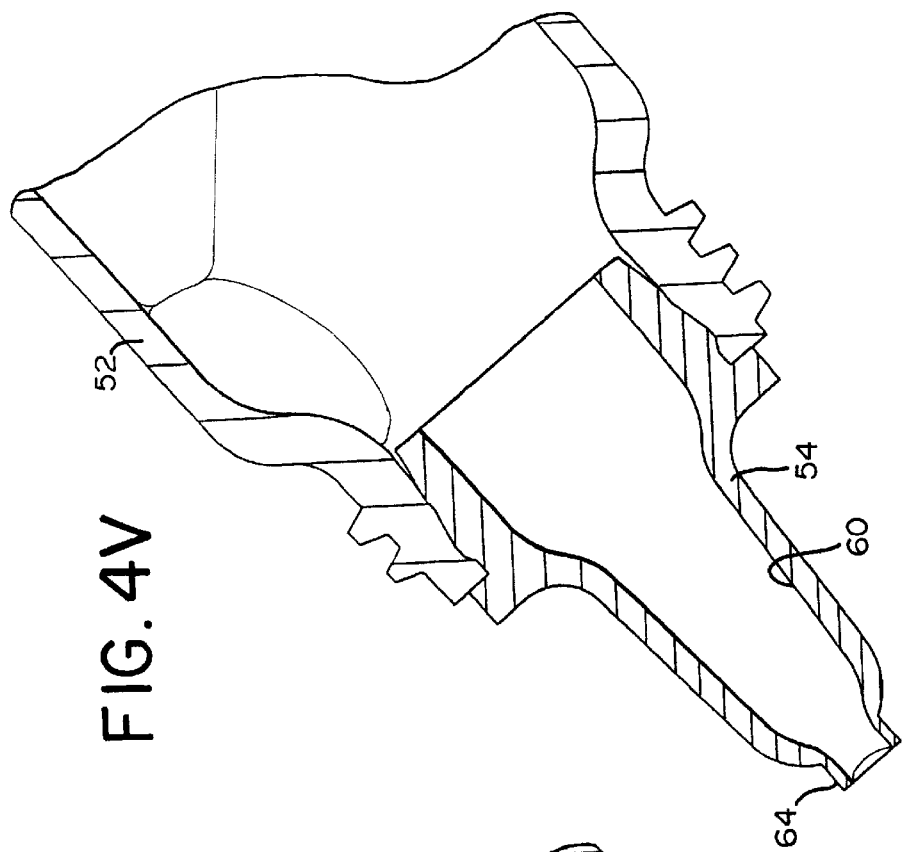
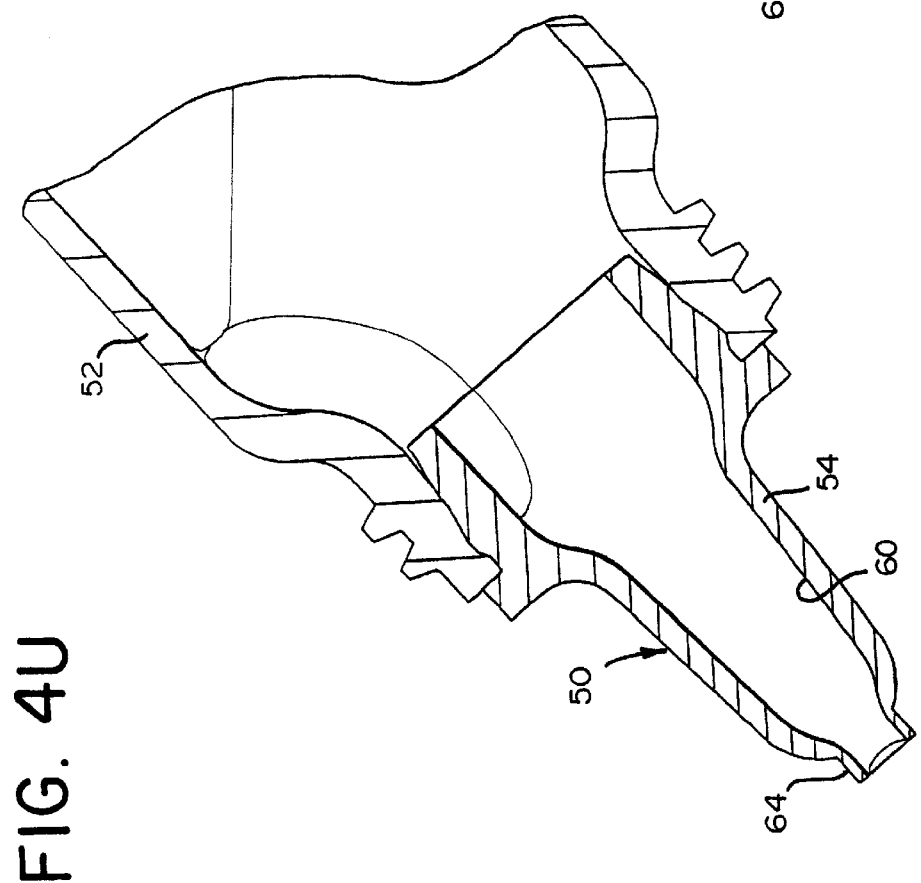

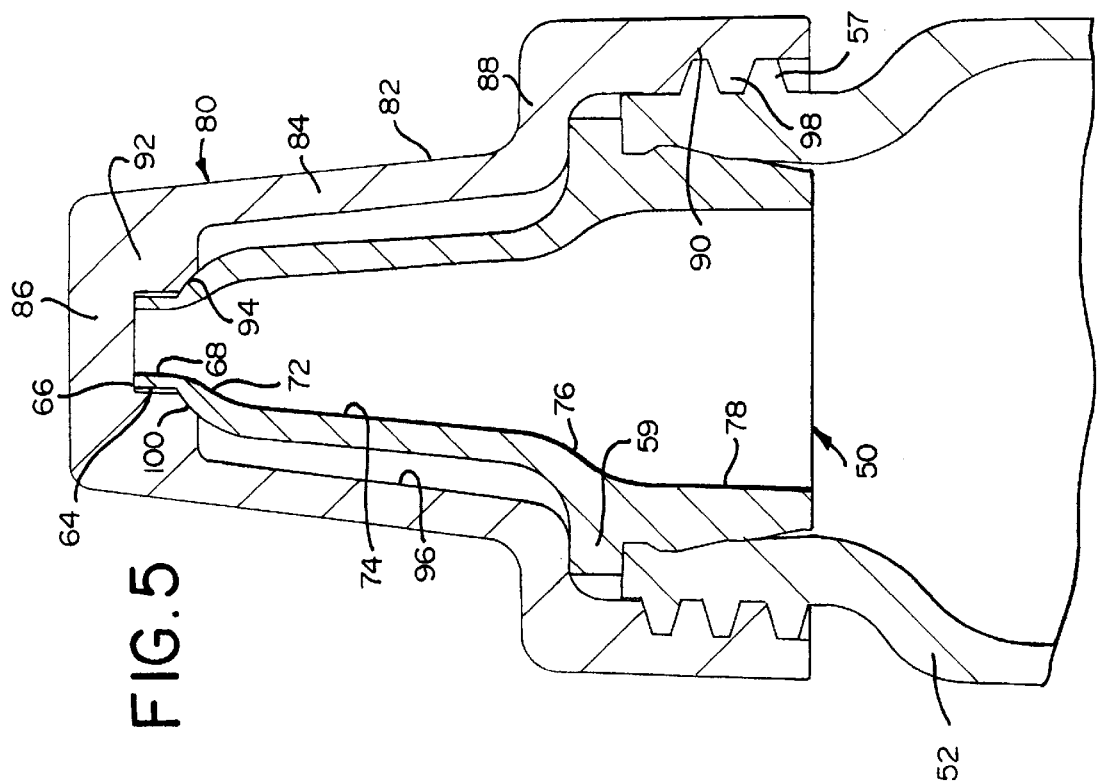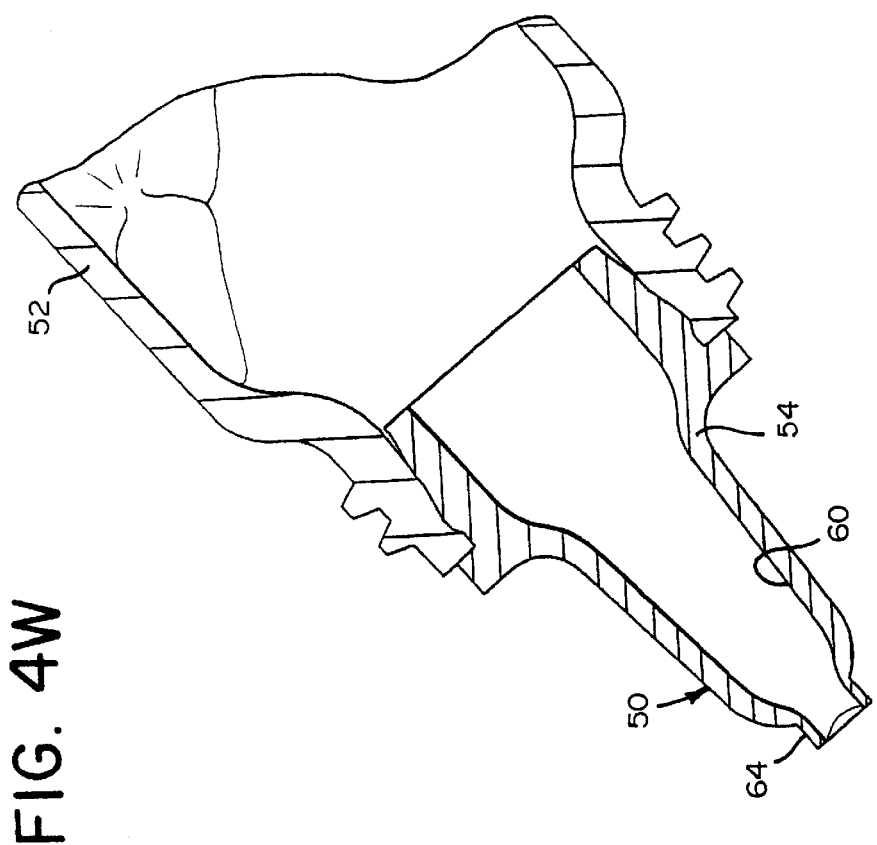

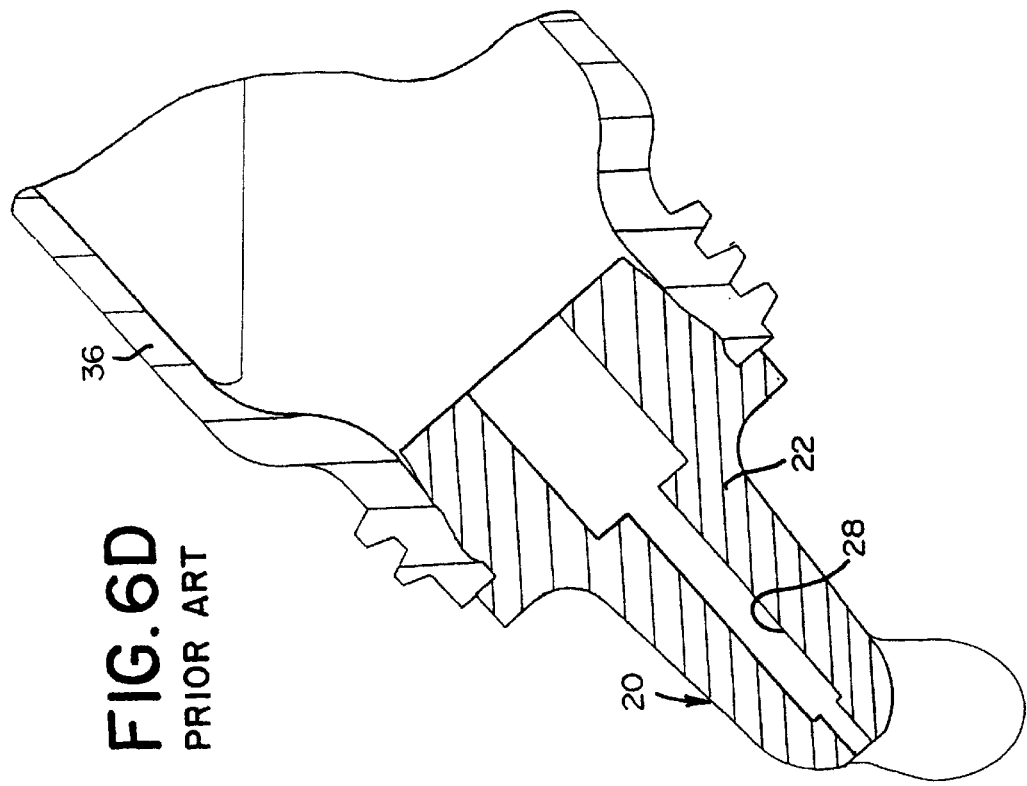
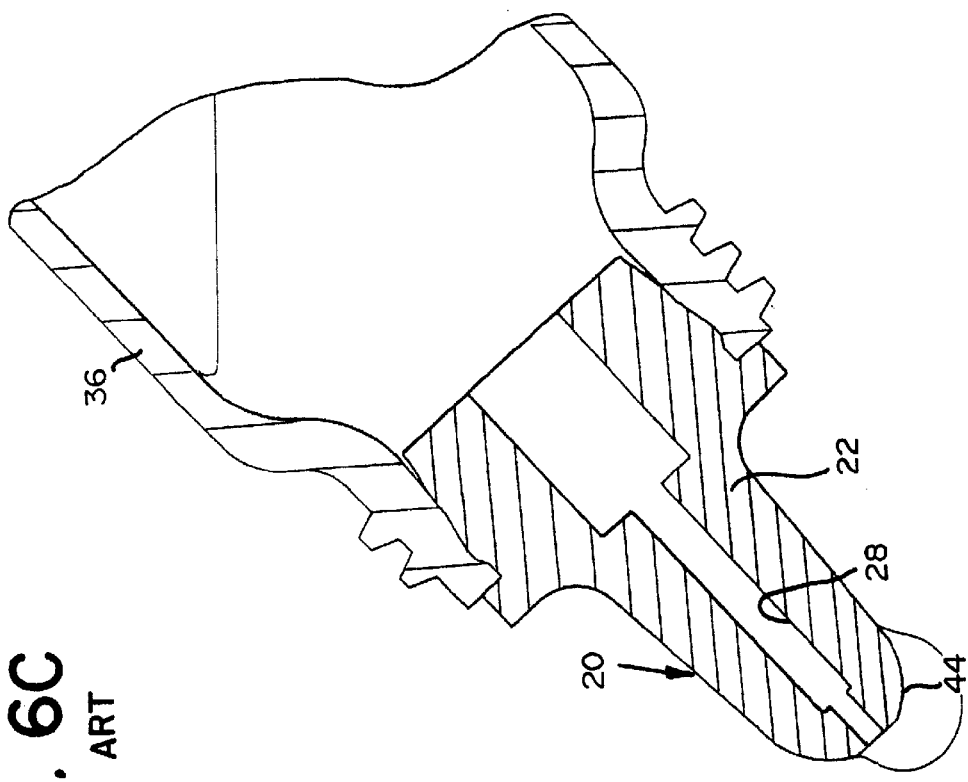

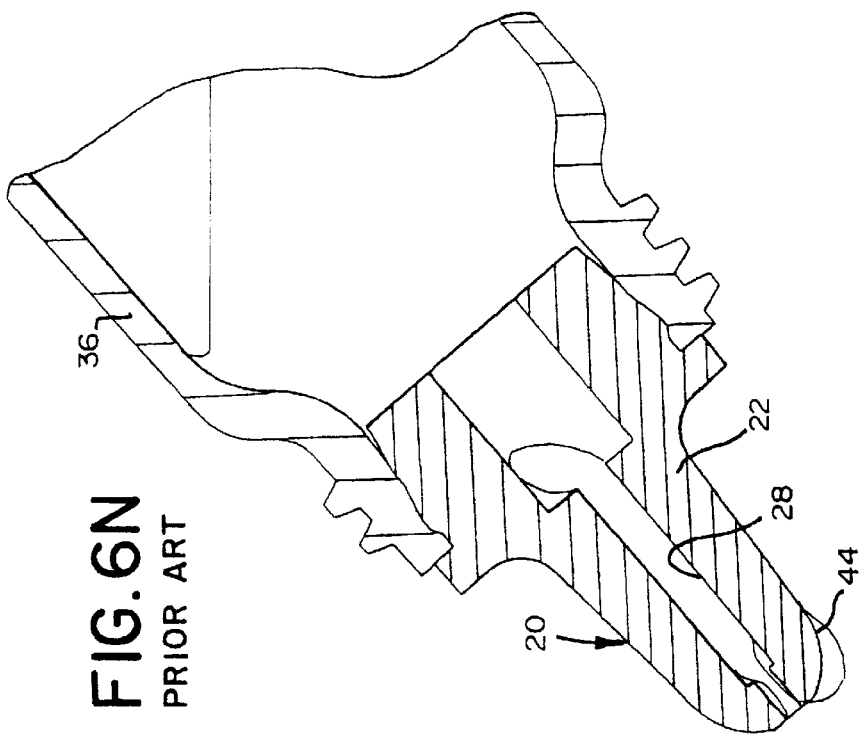
FIG. 6N PRIOR ART
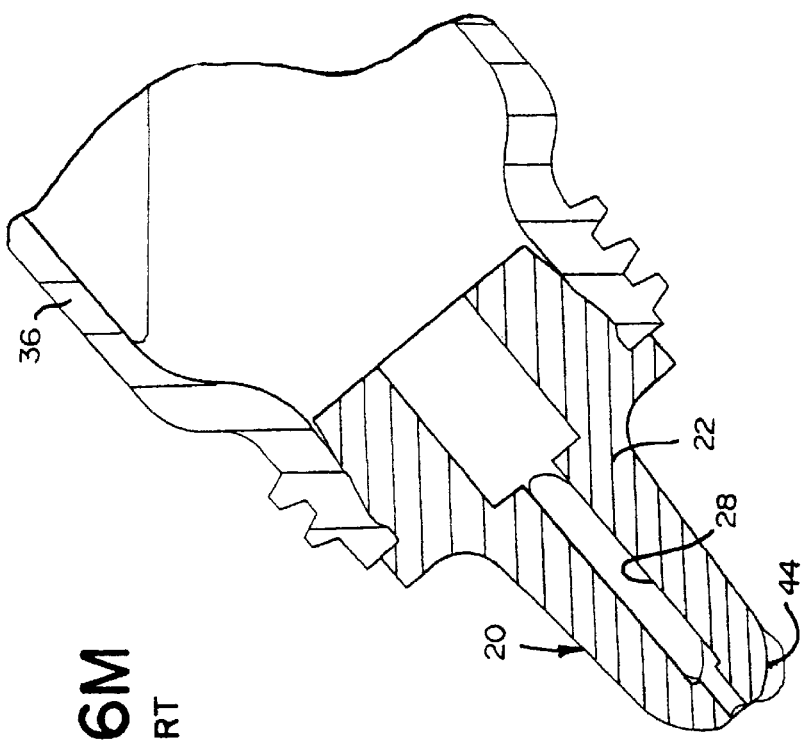
FIG. 6M PRIOR ART
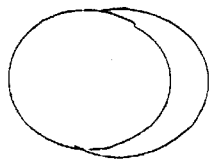

NON-BUBBLE FORMING DROPPER TIP

BACKGROUND OF THE INVENTION

This invention is generally directed to a novel non-bubble forming dropper tip which is used to dispense fluids, such as medications and the like. More particularly, the invention contemplates a novel multiple-use dropper tip which is designed to control air bubble development and drop size when the occasional bubble is encountered while dispensing viscous, low density, often thixotropic fluids, such as liquid eye medications or the like.

In order to allow less frequent user applications and reduced rate of absorption by the body, medications for the eye are increasingly being formulated to provide sustained release into the eye. Viscous high film strength carrier vehicles used to deliver these medications can make uniform dose delivery by means of common, prior art dropper bottles difficult. These medications may be highly disposed to inadvertent generation of air bubbles, which in turn accumulate at the meniscus or even trap within the fluid body. These bubbles are often very reluctant to disperse once they have been formed.

A depiction of dispensing drops from a prior art dropper tip 20 is shown in FIGS. 6A–6Q. The dropper tip 20 is formed from a body 22 having an inner wall 24 which defines a conduit therethrough. The conduit is formed from a first cylindrical wall portion 26, which is connected to a larger diameter second cylindrical wall portion 28, which is connected to an even larger diameter third cylindrical wall portion 30. The transition between the first and second wall portions 26, 28 is not smooth and a sharp shoulder 32 is provided. Likewise, the transition between the second and third wall portions 28, 30 is not smooth and a sharp shoulder 34 is provided.

Bubble generation most often occurs during the aspiration phase of dispensing when the make-up air drives fluid back down the dropper tip 20 into the container 36. As is shown in FIGS. 6A–6Q, air returning quickly back down the conduit and encountering the sharp shoulders 32, 34 of the smaller-to-larger diameter transitions can cause bubbles to be formed if a film bridges across this transition edge resulting in a film covered aperture upon which the inrushing air will cause bubbles to be blown. Bubbles must be kept from blocking outward fluid flow paths where the bubbles can become entrained in the fluid and impair accurate drop formation.

A second prior art dropper tip 38 is shown in FIG. 7. This dropper tip 38 is formed from a body 40 having an inner wall 42 which defines a conduit therethrough. The conduit is straight and has a small diameter.

Conduit diameter is also important in controlling bubbles. A conduit which has a diameter that is too small will exhibit jetting and bubbling aspiration as shown in the prior art dropper tip 38 shown in FIG. 7

Moreover, in each of these prior art dropper tips 20, 38, the delivery tip surface 44 is rounded. The rounded surface 44 encourages the attachment of fluid thereto which can interfere with proper drop size, see FIGS. 6A–6Q.

The present invention provides a novel dropper tip structure which overcomes these problems and presents other features and advantages over the prior art which will become apparent upon a reading of the attached specification, in combination with an examination of the drawings.

OBJECTS AND SUMMARY OF THE INVENTION

A general object of the present invention is to provide a novel multiple-use dropper tip which is designed to control air bubble development and drop size when the occasional bubble is encountered while dispensing viscous, low density, often thixotropic fluids, such as liquid eye medications or the like.

An object of the present invention is to provide a novel dropper tip having a delivery tip which controls drop size to promote limited momentary attachment of fluid thereto when fluid is being dispensed from the dropper tip.

Another object of the present invention is to provide a novel dropper tip having a delivery tip which discourages fluid wetting and migration beyond the designated perimeter of the delivery tip.

Yet another object of the present invention is to provide a novel dropper tip having an inner wall which discourages fluid wetting thereof.

A further object of the present invention is to provide a novel dropper tip having an inner wall defining a conduit which is designed to encourage fluid detachment from the inner wall whenever the fluid is caused to flow away from the delivery tip back toward the container, such as after drops have been dispensed and the squeezed container has been released to aspirate make-up air.

Yet a further object of the present invention is to provide a novel closure cap for sealing the dropper tip of the present invention.

Briefly, and in accordance with the foregoing, the present invention discloses a multiple-use dropper tip which is designed to control air bubble development and drop size when bubbles are encountered while dispensing fluids, such as liquid eye medications or the like. The dropper tip is connected to a squeezable container having the fluid therein and is used to dispense the fluid therefrom in a controlled manner.

The dropper tip is formed from a body having first and second opposite ends and an inner wall defining a conduit therethrough. The inner wall smoothly diverges and gradually increases in inner diameter from the first end to the second end such that air bubbles are prevented from being trapped along the inner wall. That is to say, the inner wall defining the conduit does not have any sharp corners or steps therein upon which fluid could bridge and form bubbles. The body inner wall is highly polished and may be made of olefinic material, silicone rubber material, or fluorocarbons, including, but not limited to, polytetrafluoroethylene (PTFE), carbon tetrafluoroethylene (CTFE), fluoroethylene propylene (FEP) or the like, to resist fluid wetting, facilitate fluid detachment therefrom and to reduce fluid film thickness therealong. The surface of the inner wall is smoothed to minimize surface roughness. A tubular portion having a flat end is provided at the first end of the body to promote limited momentary attachment of fluid thereto when fluid is being dispensed from the dropper tip. A sharp outer perimeter edge is provided by the flat end to provide an instant transition to discourage fluid wetting and migration beyond the designated perimeter of the flat end.

A novel closure cap is provided for sealing the dropper tip of the present invention. The closure cap seals the dropper tip at two places to prevent the entrance of contaminants therein.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a side elevational view of a novel dropper tip which incorporates the features of the present invention;

FIG. 2 is a cross-sectional view of the dropper tip shown in FIG. 1 attached to a container which is shown partially in cross-section;

FIG. 3 is a top elevational view of the dropper tip shown in FIG. 1;

FIGS. 4A–4G are cross-sectional views of the dropper tip shown in FIG. 1 attached to a container, which is shown partially in cross-section, showing a first drop formation and release;

FIGS. 4H–4J are cross-sectional views of the dropper tip shown in FIG. 1 attached to a container, which is shown partially in cross-section, showing a first aspiration and bubble "parking";

FIGS. 4U–4W are cross-sectional views of the dropper tip shown in FIG. 1 attached to a container, which is shown partially in cross-section, showing a large bubble migration into the container;

FIG. 5 is a cross-sectional view of a novel closure cap secured to the container to which the novel dropper tip shown in FIG. 1 is attached;

FIGS. 6A–6F are cross-sectional views of a prior art dropper tip attached to a container, which is shown partially in cross-section, showing a first drop formation and release;

FIGS. 6J–6M are cross-sectional views of the prior art dropper tip attached to a container, which is shown partially in cross-section, showing a second drop formation with attached bubble due to trapped air;

FIGS. 6N and 6O are cross-sectional views of the prior art dropper tip attached to a container, which is shown partially in cross-section, showing a second aspiration and air trapping;

DETAILED DESCRIPTION OF THE ILLUSTRATED EMBODIMENT

Figure 4J:
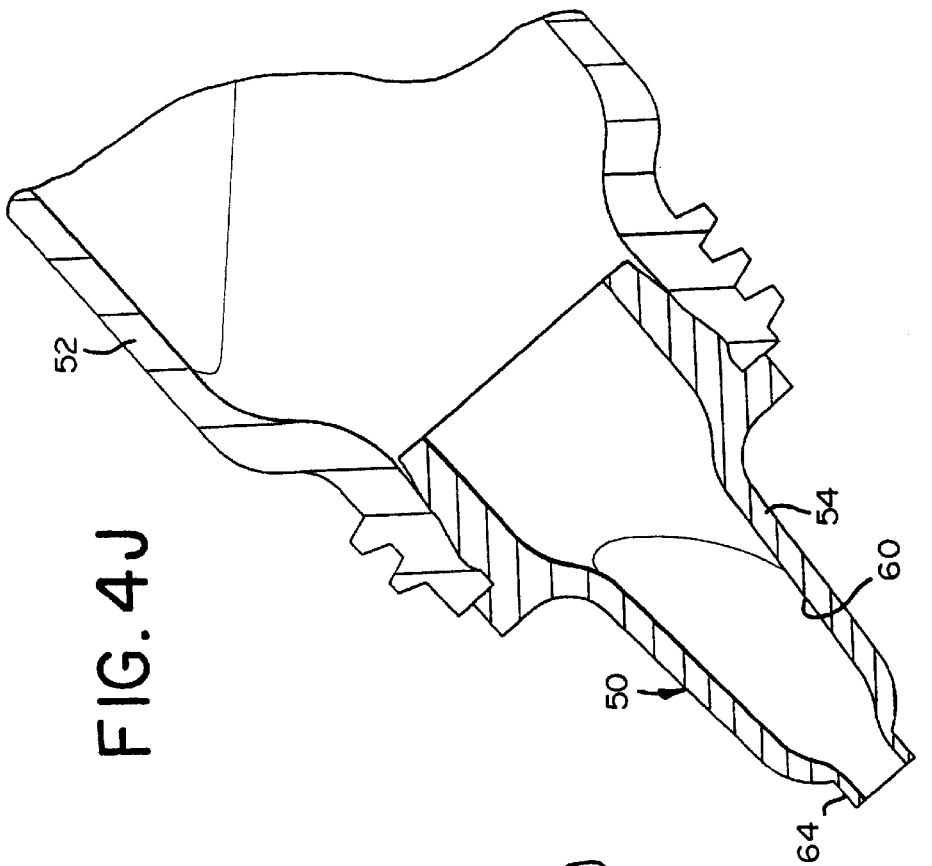
Figure 4I:
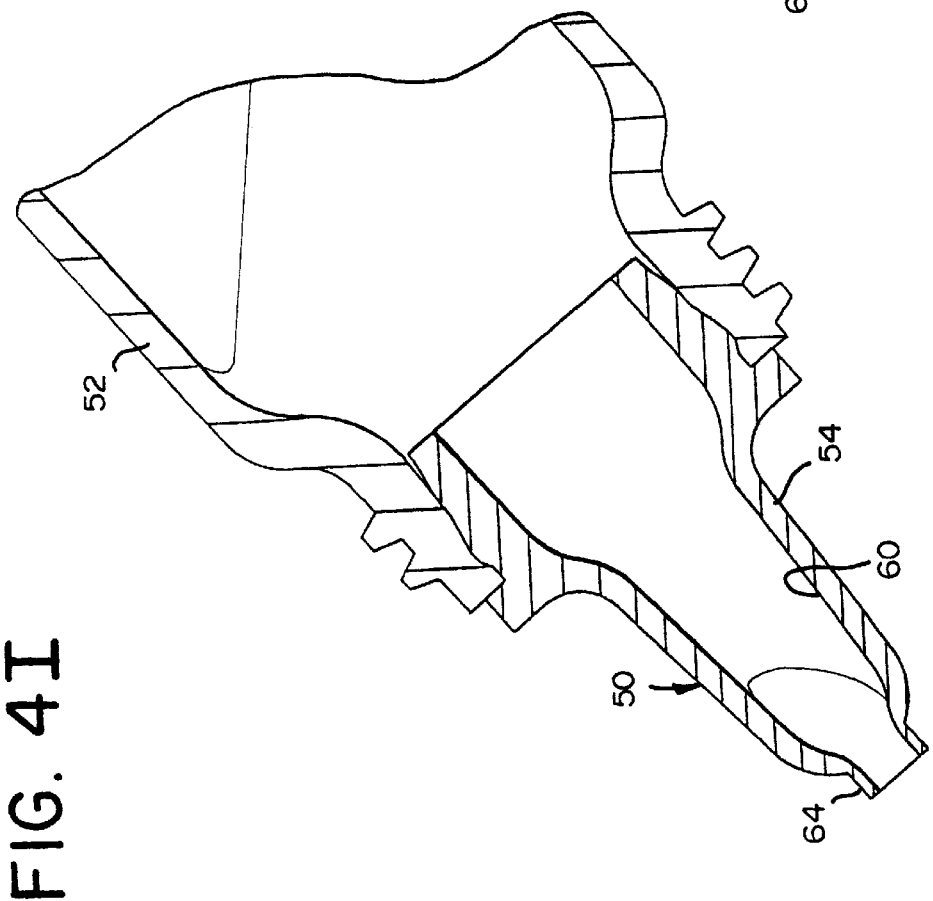
Figure 4L:
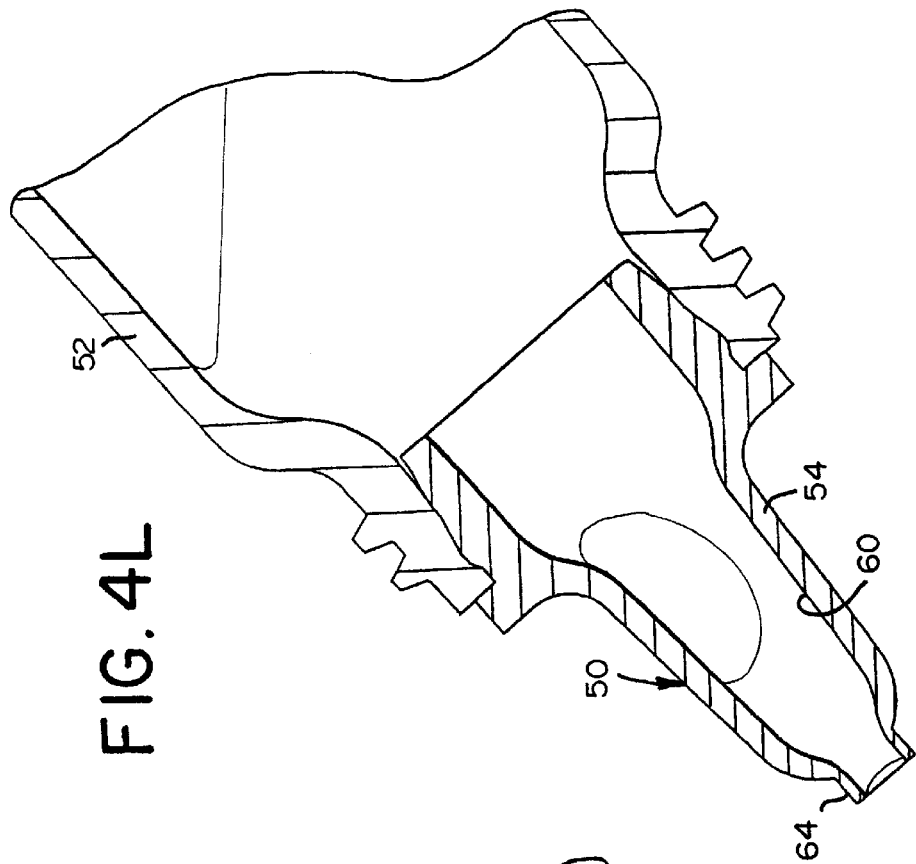
FIGS. 4K and 4L are cross-sectional views of the dropper tip shown in FIG. 1 attached to a container, which is shown partially in cross-section, showing the bubble at rest.
Figure 4K:
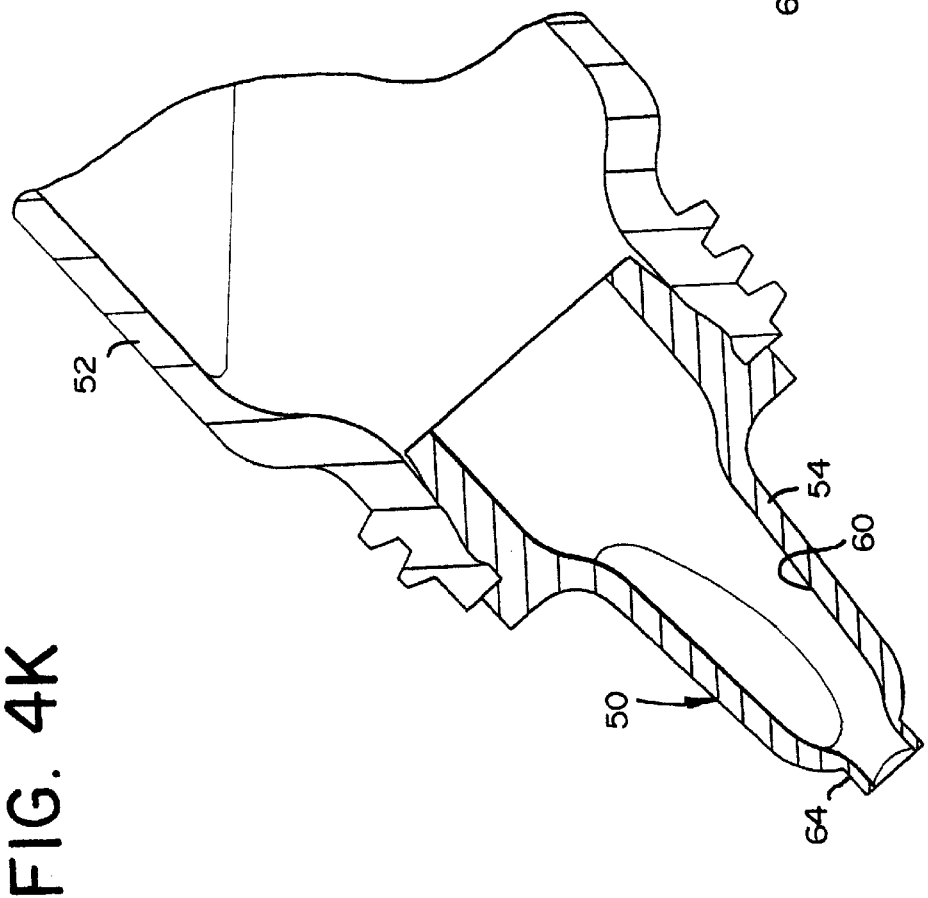
Figure 4N:
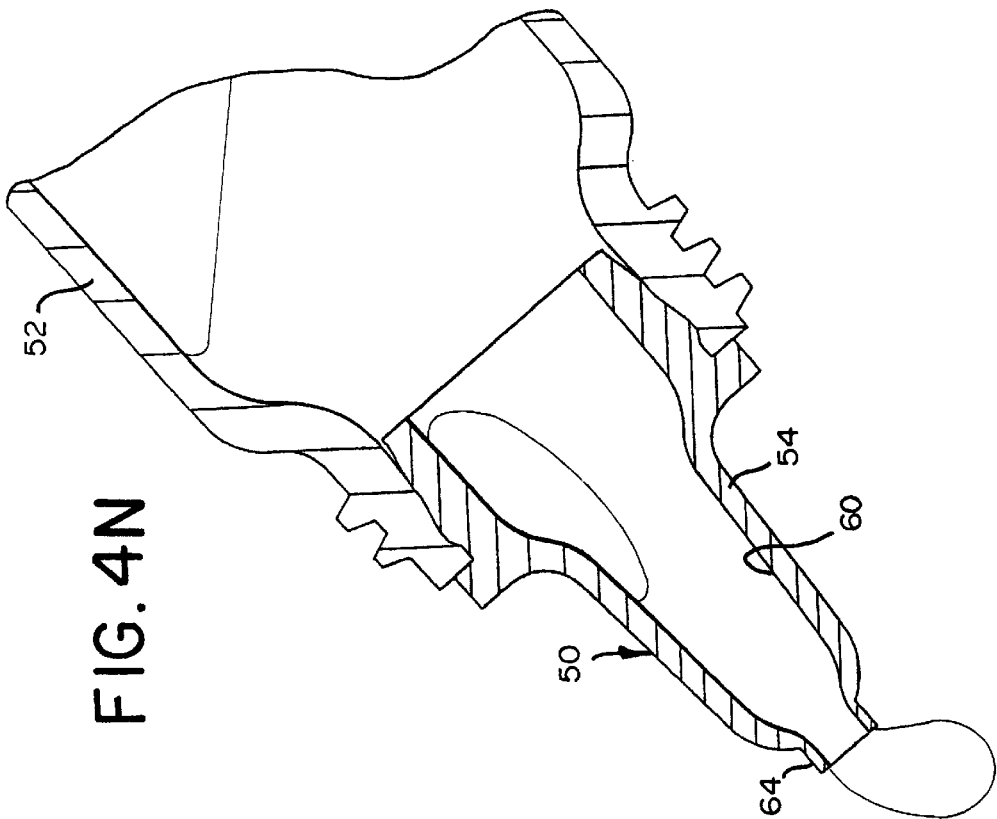
FIGS. 4M–4P are cross-sectional views of the dropper tip shown in FIG. 1 attached to a container, which is shown partially in cross-section, a second drop formation and release.
Figure 4M:
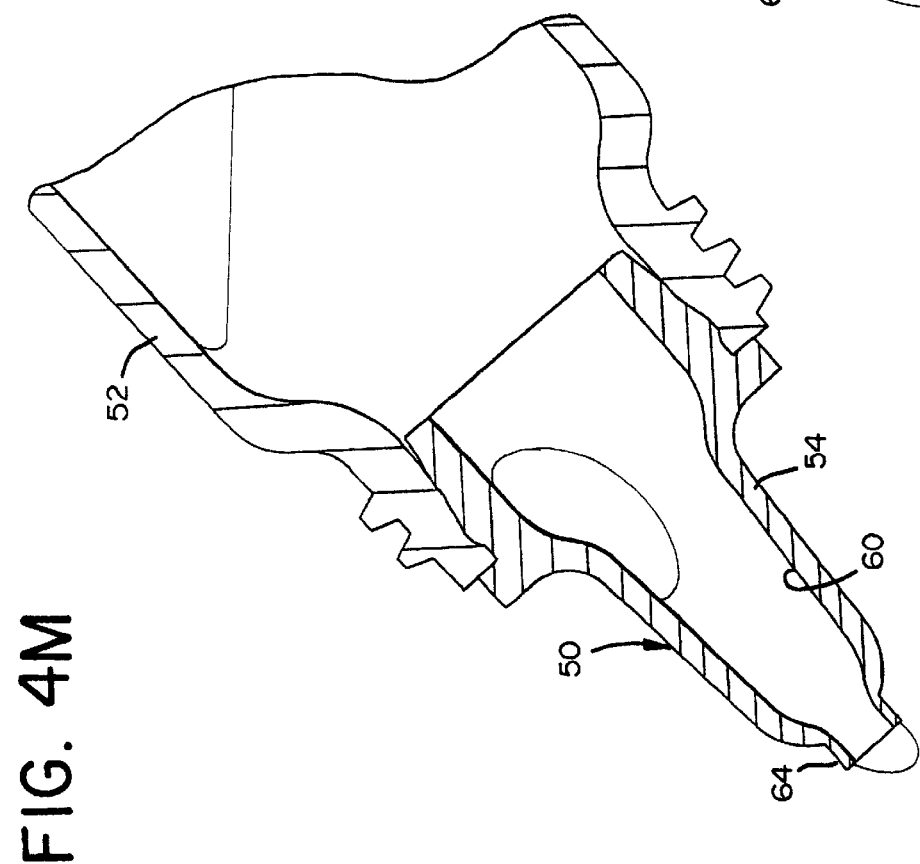
Figure 4O:
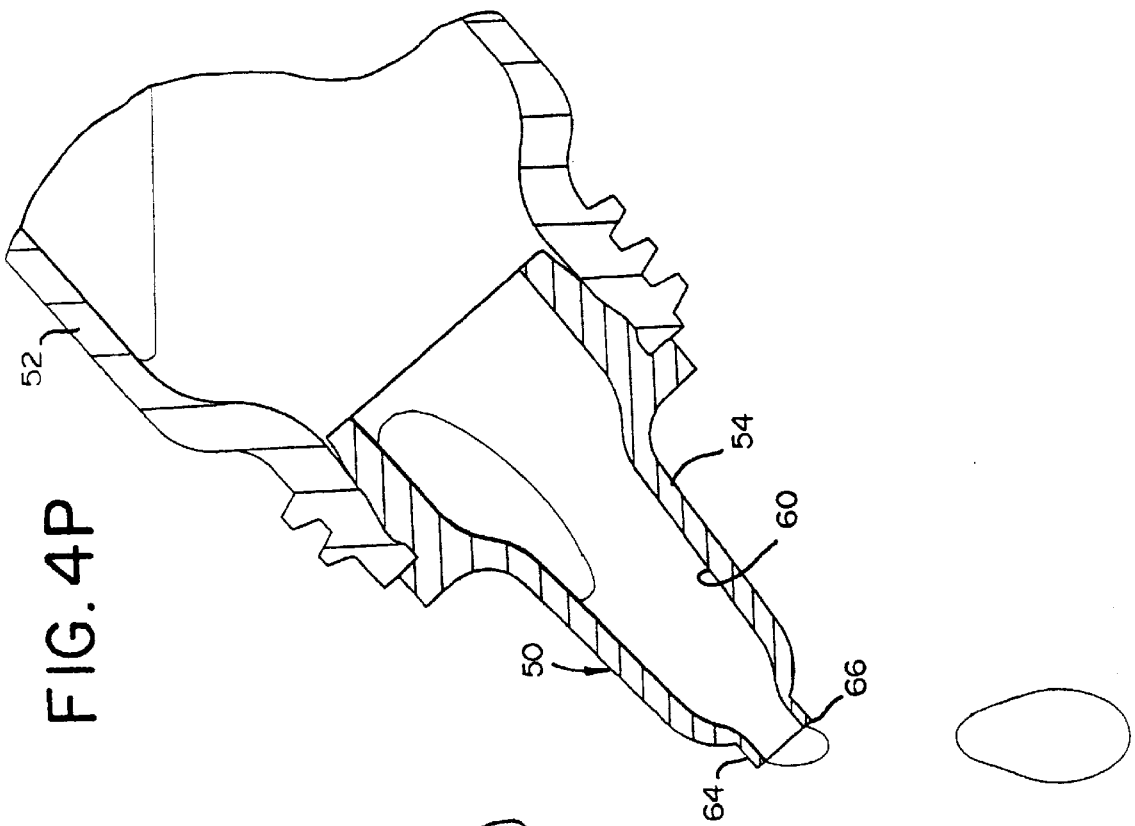
Figure 4P:
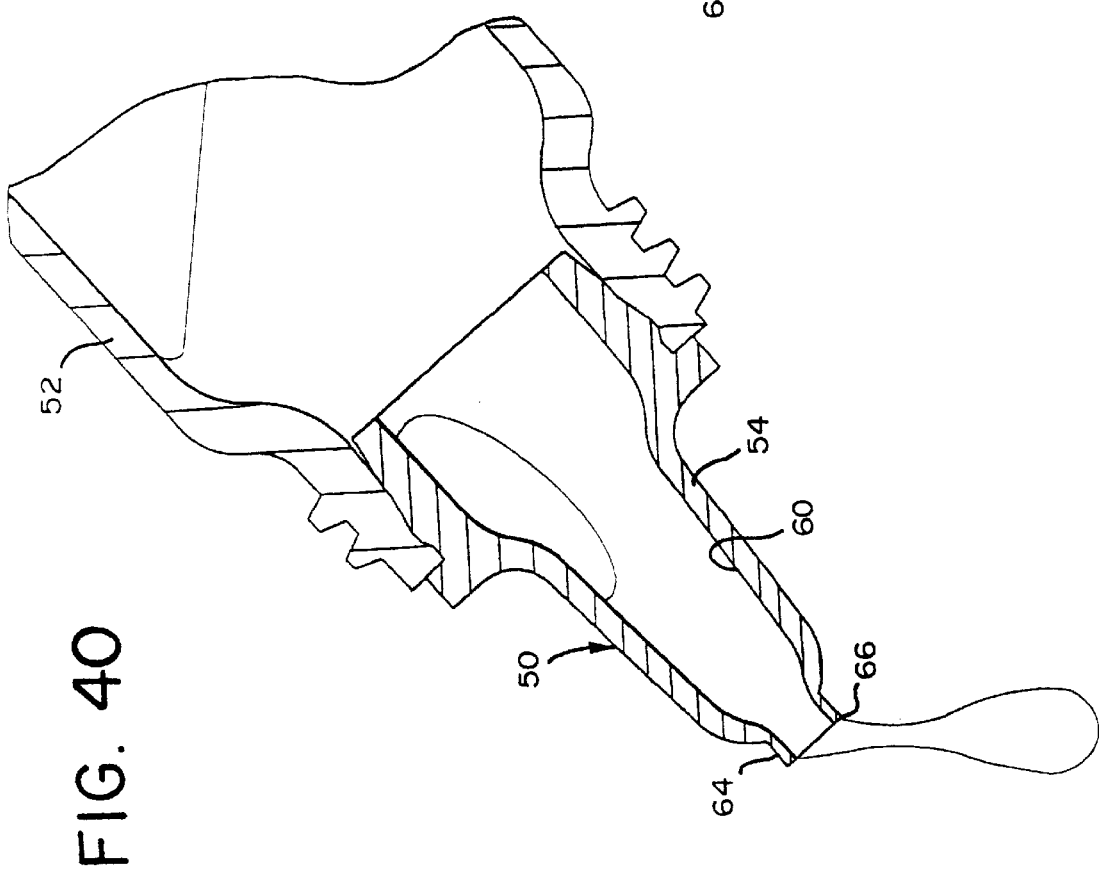
Figure 4R:
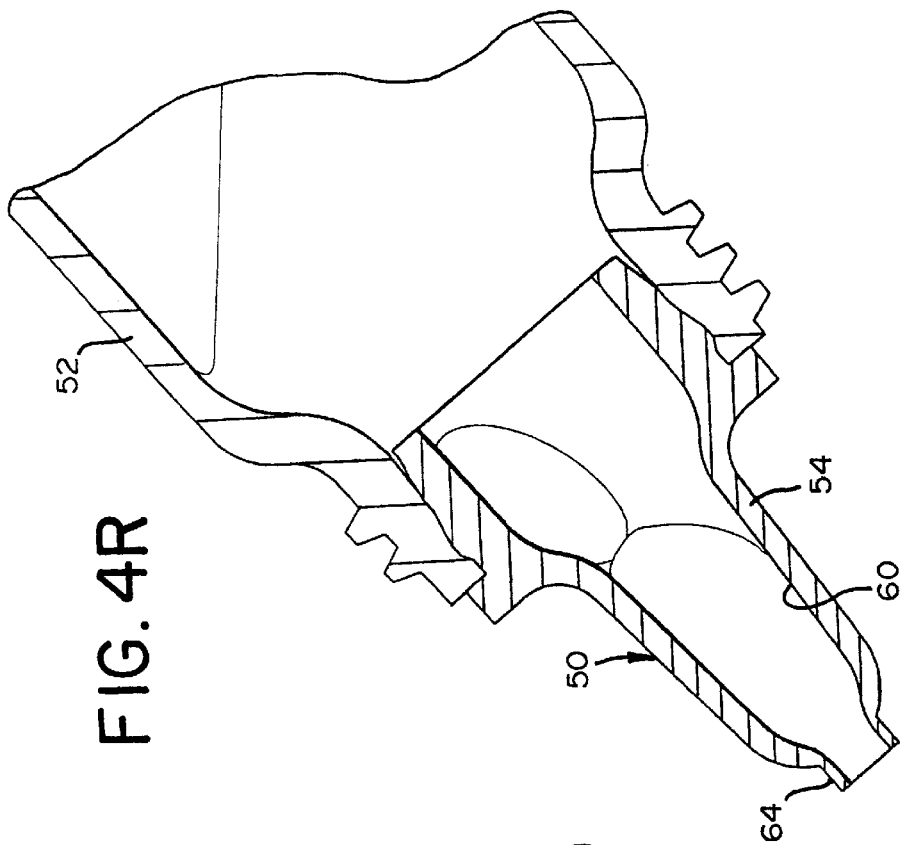
FIGS. 4Q and 4R are cross-sectional views of the dropper tip shown in FIG. 1 attached to a container, which is shown partially in cross-section, showing a second aspiration.
Figure 4Q:
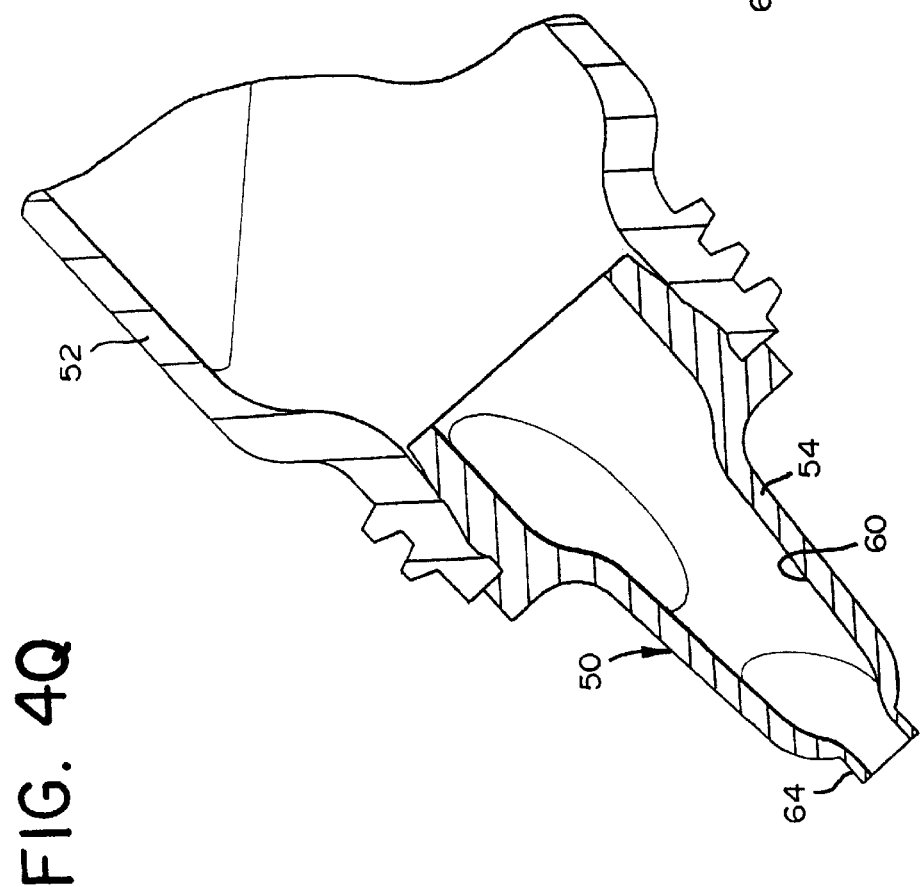
Figure 4T:
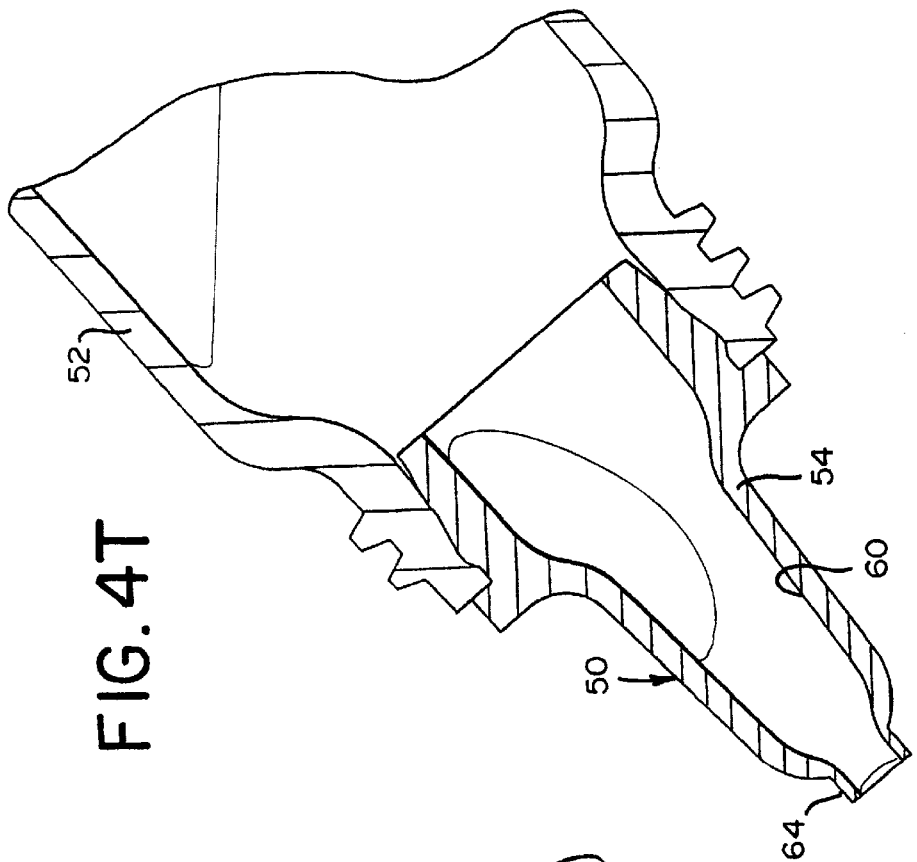
FIGS. 4S and 4T are cross-sectional views of the dropper tip shown in FIG. 1 attached to a container, which is shown partially in cross-section, showing the bubbles at rest with successive bubbles joining together to form a single bubble.
Figure 4S:
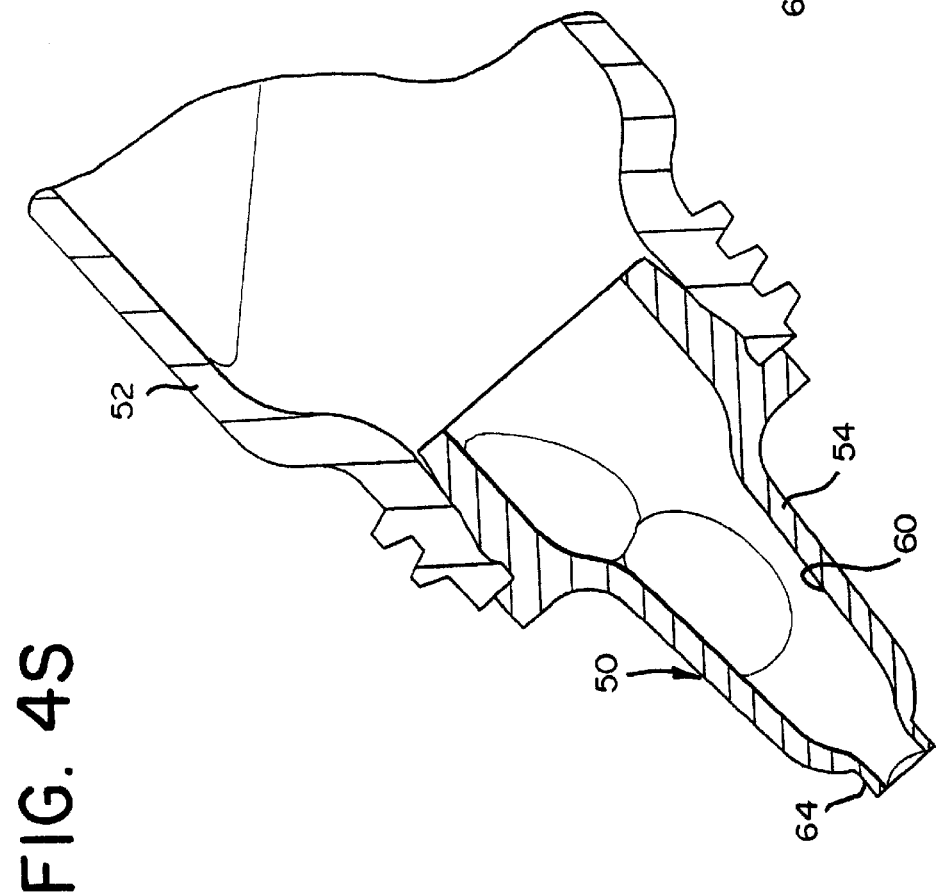

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

As shown in the drawings, the present invention provides a multiple-use dropper tip 50 which is designed to control air bubble development and drop size when the occasional bubble is encountered while dispensing viscous, low density, often thixotropic fluids, such as liquid eye medications or the like. The dropper tip 50 is connected to a conventional squeezable plastic container 52 having the fluid therein and is used to dispense the fluid therefrom.

The squeezable plastic container 52 is formed from a body 53 having an open mouth 55 and an opposite closed end (not shown). Threads 57 are provided proximate to the mouth 55 of the container 52 on the exterior of the body 53.

The dropper tip 50 is formed from a body 54 having first and second opposite ends 56, 58 and an inner wall 60 defining a conduit therethrough. The inner wall 60 provided through the body 54 smoothly diverges and gradually increases in inner diameter from the first end 56 to the second end 58 such that air bubbles are prevented from being trapped along the inner wall 60. Because of this novel structure, sharp corners, sharp edges or pockets along the length of the inner wall 60 on which air bubbles could catch as can occur in the prior art, are eliminated in the present invention. In addition, the elimination of sharp corners, edges and pockets along the inner wall 60 help prevent the break-up of large bubbles into smaller ones and this elimination does not leave a place for bubbles to attach and re-enter the fluid flow during the next dispensing.

The exterior surface of the body 54 generally follows the shape of the inner wall 60. Structure 62 is provided at the second end 58 of the body 54 along the exterior thereof for releasably attaching the body 54 within the open mouth 55 of the container 52. A circular shoulder 59 is provided on the exterior of the body 54 at a predetermined distance from the second end 58 of the body 54 and proximate to the structure 62 for reasons described herein.

A tubular delivery tip 64 having a flat end surface 66 is provided at the first end 56 of the body 54. The flat end surface 66 of the delivery tip 64 controls drop size by providing an end flat of finite frontal area to promote limited momentary attachment of fluid thereto when fluid is being dispensed from the novel dropper tip 50 of the present invention. The tubular delivery tip 64 defines a cylindrical wall portion 68 of the inner wall 60. As shown in the drawings, the wall portion 68 is generally cylindrical, however, it is to be understood that the wall portion 68 may gradually diverge from its first end to its second end. The outer perimeter of the flat end surface 66 provides a sharp perimeter edge 70 to provide an instant transition to discourage fluid wetting and migration beyond the designated perimeter of the flat end surface 66.

In prior art dropper tips, designers often utilize the final outlet passageway diameter as a control feature to attempt to limit drop size. This has more impact in dispensing from totally upside down than the more traditional 45° dispensing, but it is used. In general, a smaller bore yields a smaller drop at 90°. With the high viscosity, low density materials as used in the present invention, a small bore will aggravate jetting, bubble forming and trapping. The flat end surface 66 which promotes limited momentary attachment of the fluid, makes reliance upon small passageways unnecessary for drop size control and eliminates the penalties of a small passageway.

The delivery tip 64 is supplied by means of the internal conduit formed by the inner wall 60 which conducts fluid, such as medication, from the interior of the affixed squeezable container 52 to the delivery tip flat end surface 66. The inner wall 60 is designed and manufactured in a manner to discourage fluid wetting thereof. In addition, the inner wall 66 is designed to encourage fluid detachment therefrom whenever the fluid is caused to flow away from the delivery tip 64 back toward the container 52, such as after drops have been dispensed and the squeezed container 52 has been released to aspirate make-up air.

The inner wall 60 further includes a first wall portion 72 having first and second opposite ends, a second wall portion 74 having first and second opposite ends, a third wall portion 76 having first and second opposite ends, and a fourth wall portion 78 having first and second opposite ends. The first end of the first wall portion 72 smoothly transitions with the second end of the cylindrical wall portion 68. The second end of the first wall portion 72 smoothly transitions with the first end of the second wall portion 74. The second end of the second wall portion 74 smoothly transitions with the first end of the third wall portion 76. The second end of the third wall portion 76 smoothly transitions with the first end of the fourth wall portion 78. The transition walls 72, 76 between the respective wall sections 68, 74, 78 are curved or arcuate and devoid of sharp corners.

The first wall portion 72 is radiused to provide a smooth transition from the second end of the cylindrical wall portion 68 to the first end of the second wall portion 74. The inner diameter of the first wall portion 72 at its first end is equal to the inner diameter of the cylindrical wall portion 68 at its second end. The inner diameter of the first wall portion 72 at its first end is smaller than at its second end.

The second wall portion 74 gradually diverges from its first end to its second end such that the inner diameter at its second end is greater than the inner diameter at its first end. The inner diameter of the second wall portion 74 at its first end is equal to the inner diameter of the first wall portion 72 at its second end.

The third wall portion 76 is radiused to provide a smooth transition from the second end of the second wall portion 74 to the first end of the fourth wall portion 78. The inner diameter of the third wall portion 76 at its first end is equal to the inner diameter of the second wall portion 74 at its second end. The inner diameter of the third wall portion 76 at its first end is smaller than at its second end.

The fourth wall portion 78 gradually diverges from its first end to its second end such that the inner diameter at its second end is greater than the inner diameter at its first end. The inner diameter of the fourth wall portion 78 at its first end is equal to the inner diameter of the third wall portion 76 at its second end.

Figure 6B:
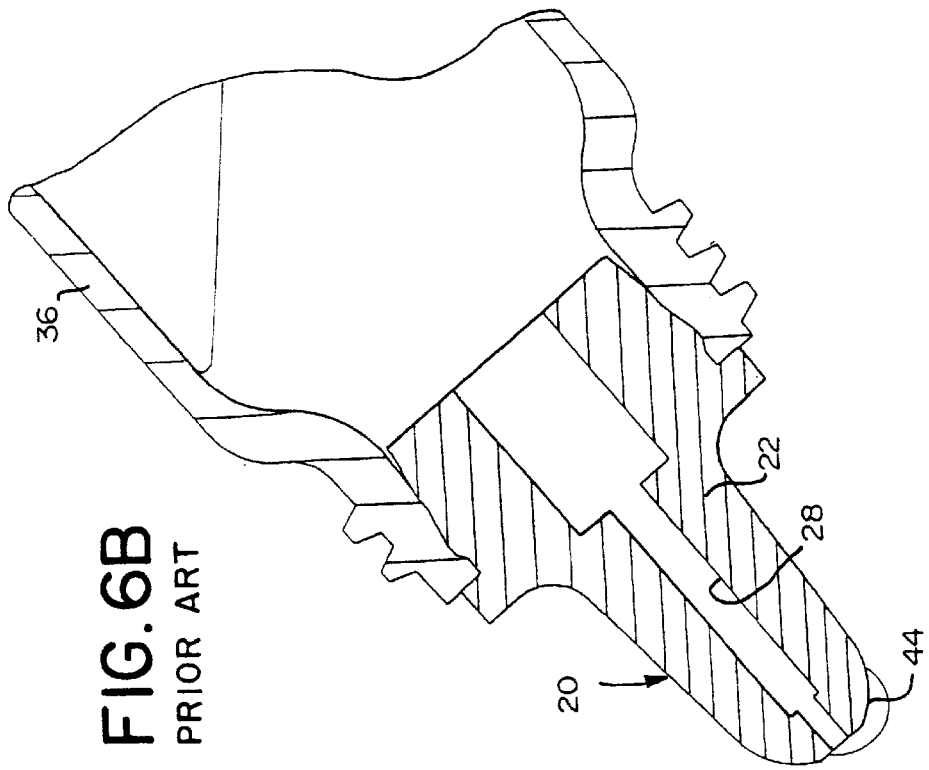
Figure 6A:
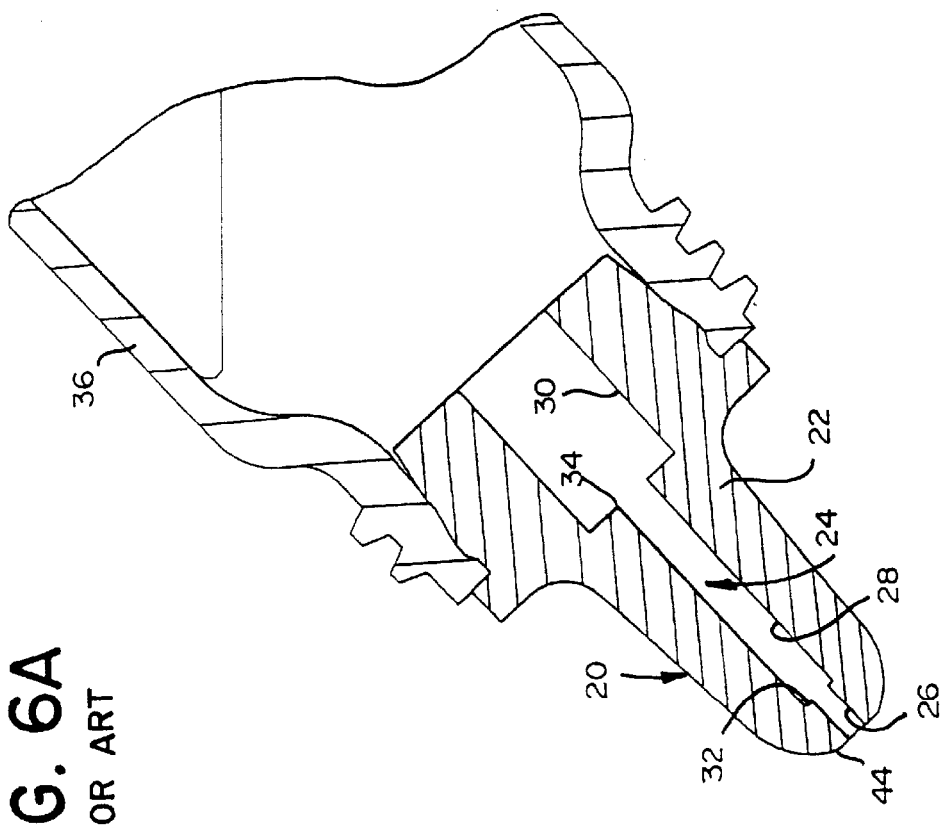
Figure 6F:
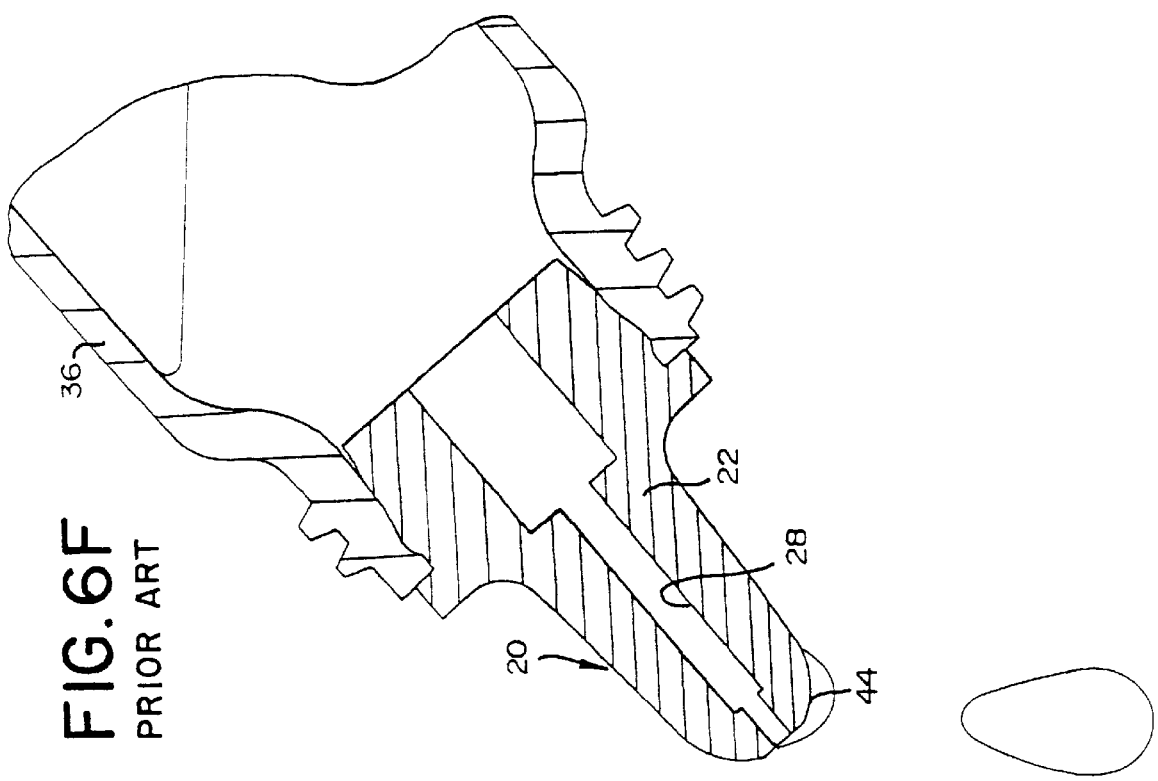
Figure 6E:
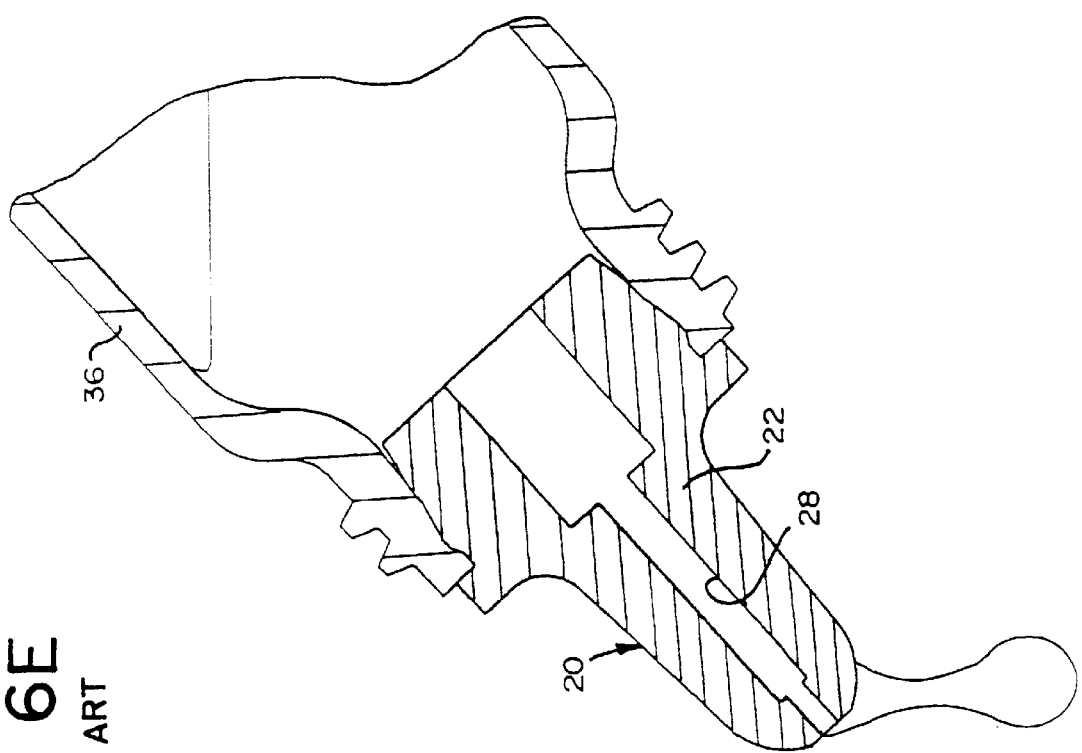
Figure 6H:
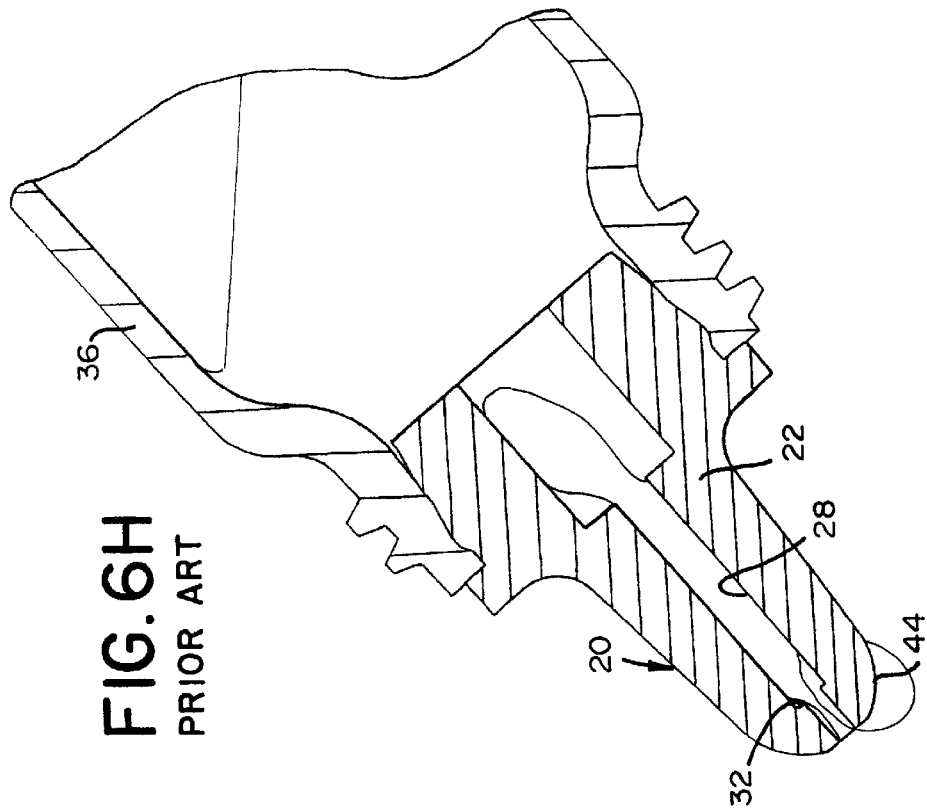
FIGS. 6G–6H are cross-sectional views of the prior art dropper tip attached to a container, which is shown partially in cross-section, showing a first aspiration and air trapping.
Figure 6G:
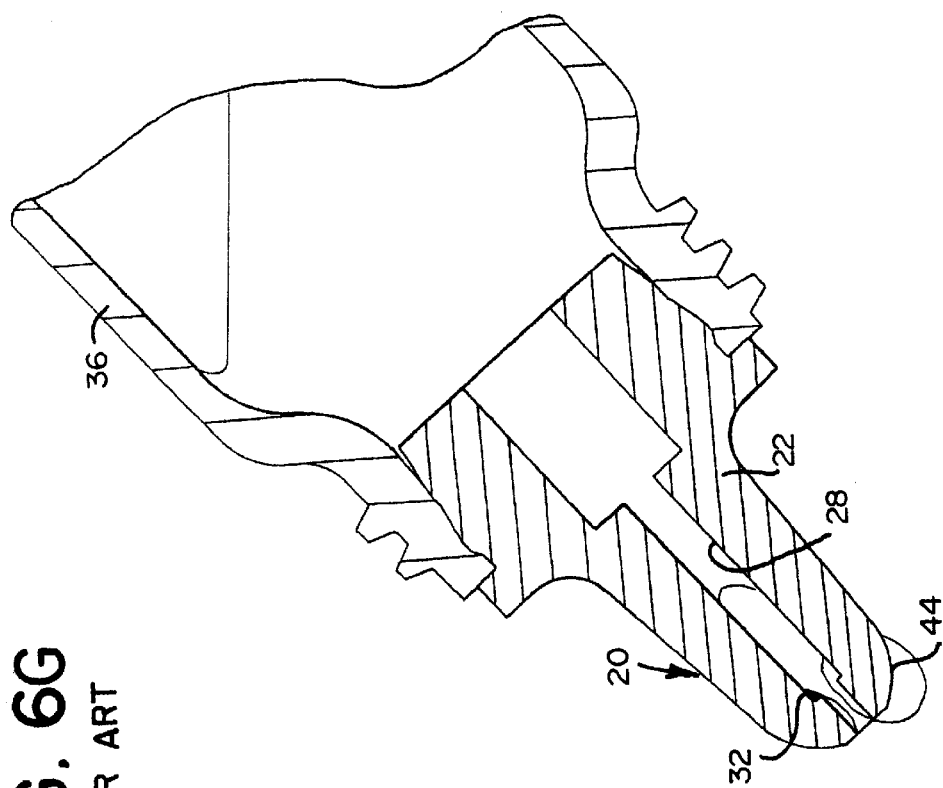
Figure 6J:
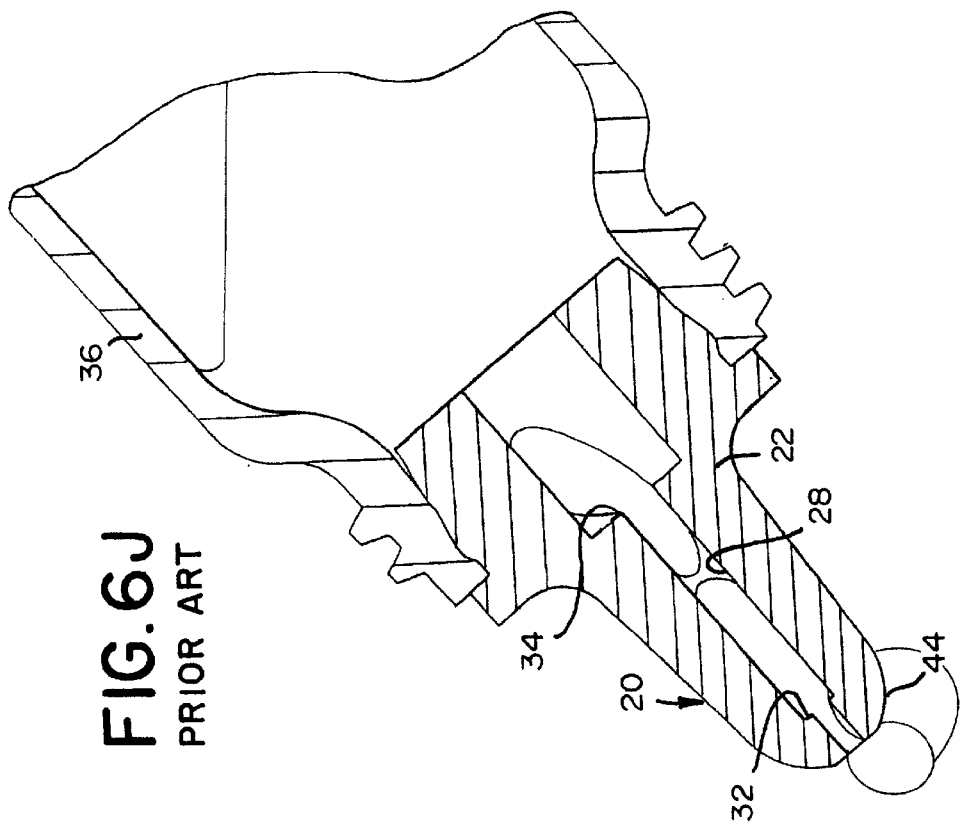
Figure 6I:
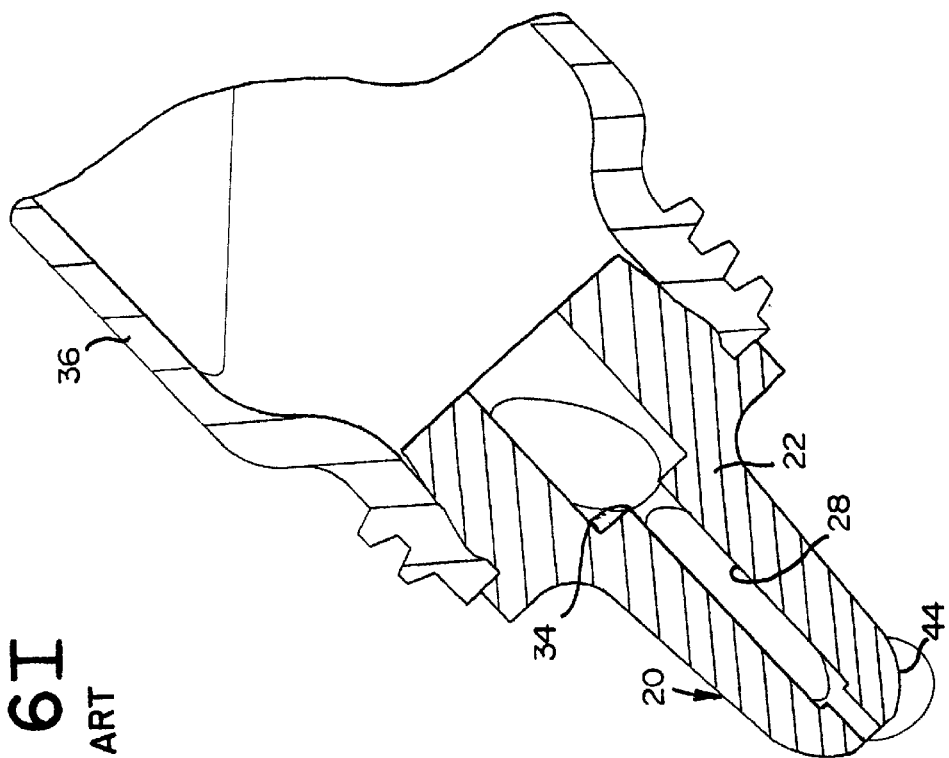
FIG. 6I is a cross-sectional view of the prior art dropper tip attached to a container, which is shown partially in cross-section, showing the bubbles at rest.
Figure 6K:
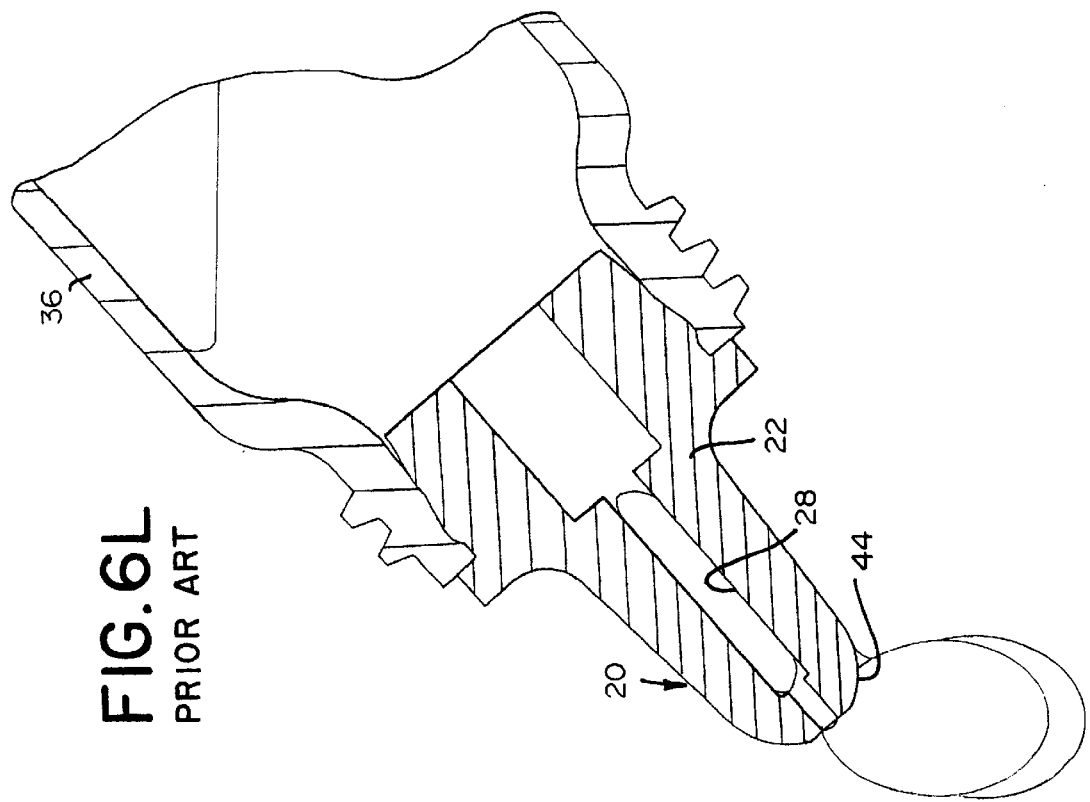
Figure 6L:
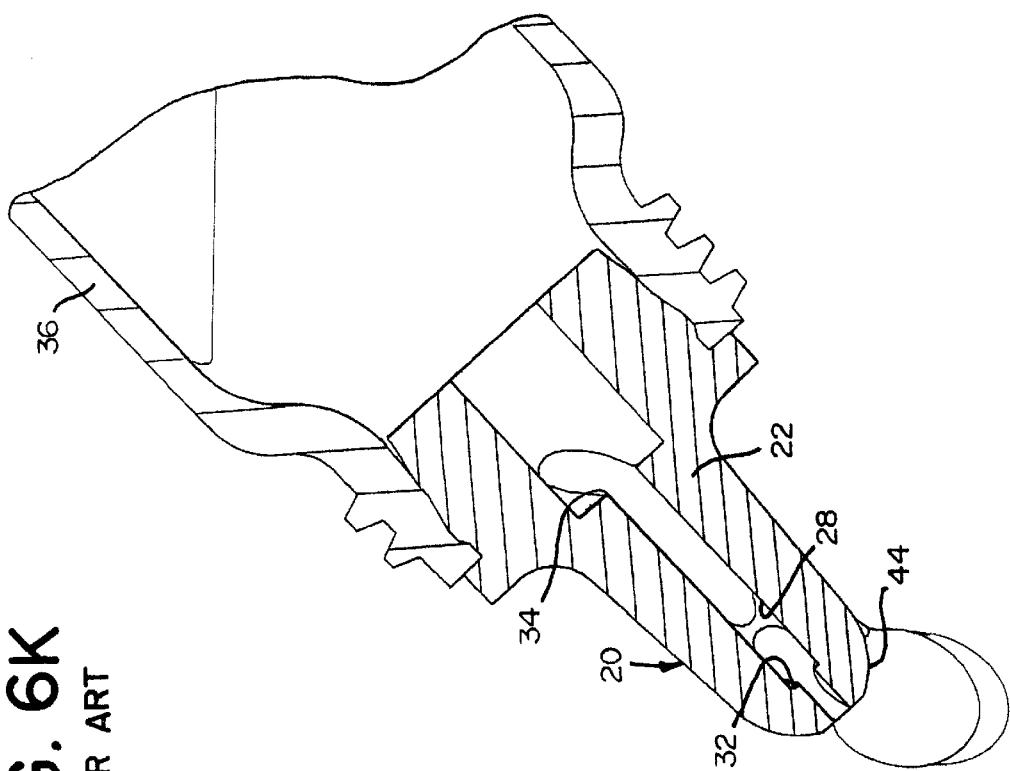
Figure 6P:
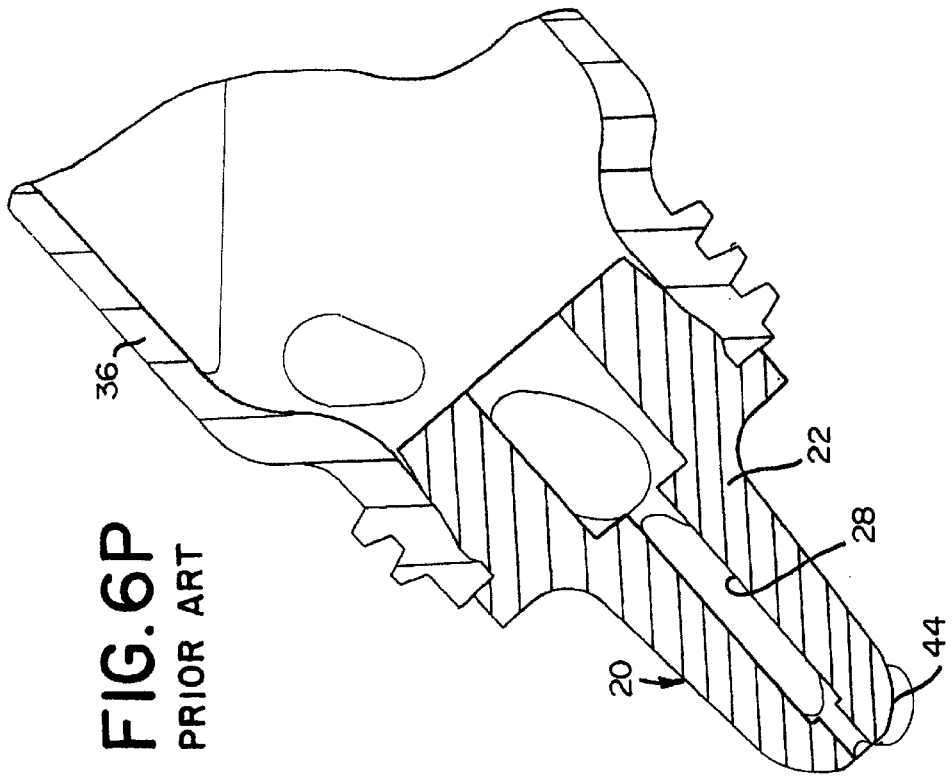
FIGS. 6P and 6Q are cross-sectional views of the prior art dropper tip attached to a container, which is shown partially in cross-section, showing a small bubble release into the container.
Figure 6O:
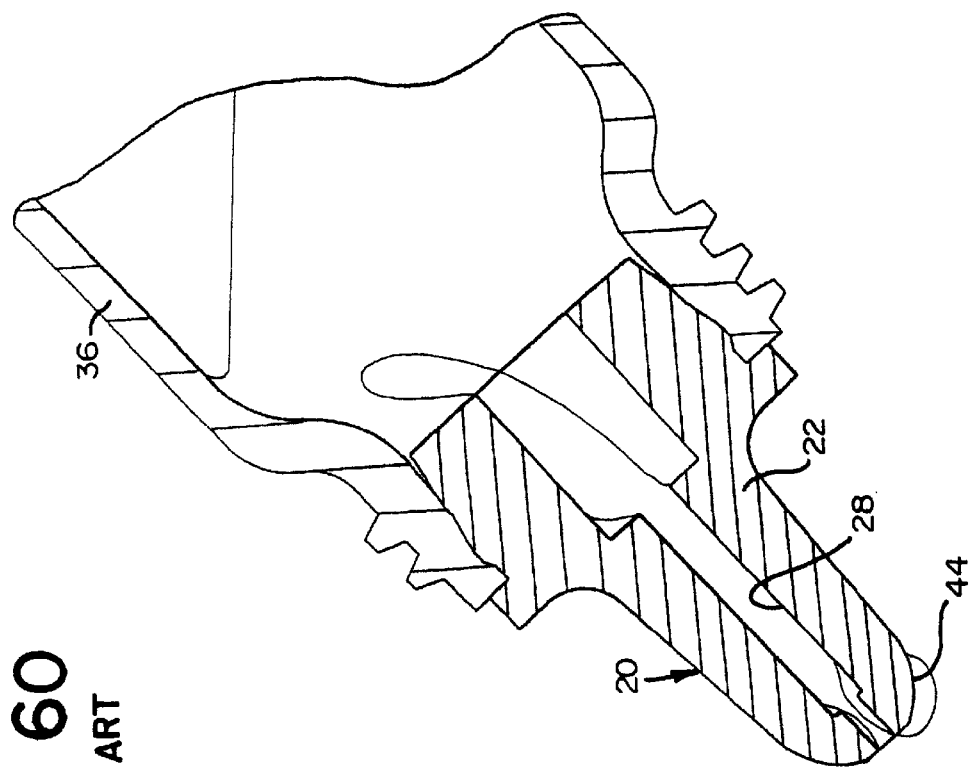
Figure 6Q:
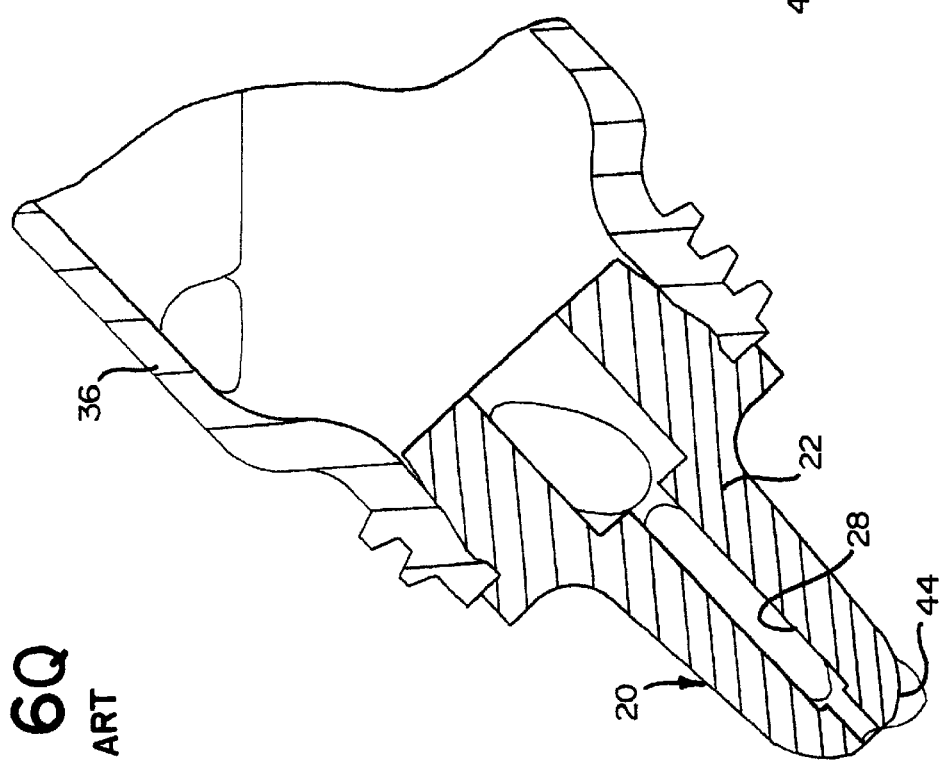

Bubble generation most often occurs during the aspiration phase of dispensing when the make-up air is sucked or drawn back into the container 52, as the wall of the container 52 is released and its inherent resiliency causes it to expand back to its original form or shape. When aspiration occurs, it tends to drive fluid back down the dropper tip 50 into the container 52. As is shown in the prior art in FIGS. 6A–6Q, air returning quickly back down the conduit and encountering sharp back side edges of any smaller-to-larger inner diameter transitions can cause bubbles to be formed if a film bridges across this transition edge resulting in a film covered aperture upon which the inrushing air will cause bubbles to be blown.

The dropper tip 50 of the present invention incorporates several structural features to reduce incidences of film forming. The generously radiused wall portions 72, 76 reduce incidences of film forming. The surface of the inner wall 60 may be highly polished and/or may be materially resistant to wetting by the fluid to improve detachment of fluid from the inner wall 60 and/or minimize impeding of the fluids retreat as incoming air forces fluid back into the container 52 during aspiration. The resultant ease of flow prevents or minimizes fluid thickness along the inner wall 60 which, in turn, inhibits bridge conditions which could lead to film bridging across the conduit. The provision of highly polished surfaces and/or use of surface materials resist fluid wetting, facilitate fluid detachment and reduce fluid film thickness along the inner wall 60. These also help to create a condition during aspiration that is inhospitable to the bubble forming process. This provides a benefit when downstream, area increasing steps within the conduit must be accommodated and its serves to prevent a washing wall of fluid from flowing and closing around the back side of the returning air flow resulting in a trapped air bubble within the returning slug of fluid.

It has been found that providing an inner wall surface of highly polished (S.P.I.-S.P.E. #1 mirror finish) olefinic material, such as DUPONT Grade 20 high density polyethylene (HDPE) or HUNTSMAN Grade 13R9A polypropylene (PP), or silicone rubber material, such as NuSIL Grade 4980 silicone rubber, provide a good passageway to resist bubble formation. To form the inner wall 60 of this material, the body 54 is also formed out of this material. A finely polished surface has less net surface area than a rougher finish. A fine surface finish also offers much shallower irregularities (but potentially many more on a microscopic level). These minute irregularities can trap air which suspends fluid and further reduces its contact with the surface. A rough surface can serve to place more surface area in contact, thereby allowing a film of fluid to puddle, cling, trap and resist flowing off. Surface roughness, regardless of material choice, may have the effect of providing microscopic shelves on which fluid can cling, thereby increasing the overall depth of fluid flow washing the inner wall, inhibiting detachment and slowing the return of the flow during aspiration. The surface of the inner wall 60 is made as smooth as possible in order to optimize resistance to bubble formation by minimizing the volume of fluid available to close behind the inrushing make-up air. The mold on which the dropper tip 50 is formed is polished to a mirror finish to make the surface of the inner wall 60 smooth when the body 54 is molded out of the chosen material. Surface material, such as TEFLON® (polytetrafluoroethylene (PTFE), carbon tetrafluoroethylene (CTFE), fluoroethylene propylene (FEP) or the like) or other fluorocarbons as a family, can be provided on the inner wall 60 or surface modifications to reduce surface wetability also provide a good passageway to resist bubble formation.

The critical surface tension of some of the materials disclosed herein are as follows:

| | |
|---|---|
| PTFE | 18 dynes/cm |
| FEP | 16 dynes/cm |
| Silicone | 24 dynes/cm |
| PE | 31 dynes/cm |
| PP | 29 dynes/cm |

The surface tension of some liquids are as follows:

| | |
|---|---|
| glycerol | 63 dynes/cm |
| silicone oils | 21 dynes/cm |
| water | 73 dynes/cm |

Wetting will occur when the surface tension of the liquid is lower than the critical surface tension of the inner wall. If the surface tension of the liquid is higher than the critical surface tension of the inner wall, the liquid will form a round droplet on the inner wall. Therefore, in the present invention, a material with a lower critical surface tension than the surface tension of the fluid is used. For example, PE (critical surface tension of 31 dynes/cm) works very well with the water based solution which can be dispensed from the present dropper tip 50. If silicone oil (surface tension of 21 dynes/cm) is used, PTFE (critical surface tension of 18 dynes/cm) or FEP (critical surface tension of 16 dynes/cm) might be used. Fluorocarbon materials provide very good critical surface tension values.

The diverging inner wall 60 cross-section assists the non-wetting process by providing space separation between opposing points on the inner wall 60 and by causing the downwashing surface fluid to spread and thin over a constantly increasing circumferential surface.

Figure 7:
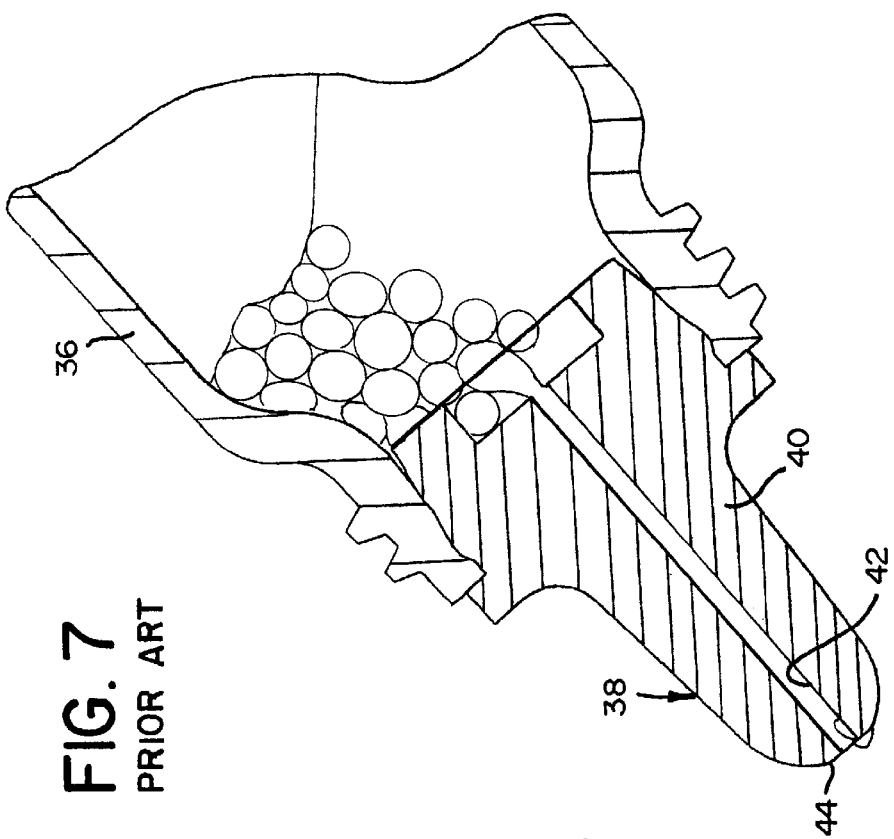
FIG. 7 is a cross-sectional view of another prior art dropper tip attached to a container, which is shown partially in cross-section, showing an aspiration and bubble formation of a small inner diameter conduit.

The size of the conduit is also important in controlling bubbles. As is shown in the prior art in FIG. 7, a conduit which is too small will exhibit jetting and bubbling aspiration. The conduit defined by the inner wall 60 of the present invention, which has larger passages having generously radiused wall portions 72, 76, is very smooth and has divergent walls 74, 78, reduces or eliminates adverse impacts of bubble formation. The dropper tip 50 of the present invention provides a safe place to "park" the inevitable bubble such that the bubble will not re-enter into outward flow during dispensing as is shown in the extreme example in FIGS. 4A–4W.

It should also be noted that in FIGS. 4Q–4T, because the body 54 has at least one enlarged diameter wall portion, an air bubble can momentarily become entrained in the fluid, but the novel shape of the conduit 60 prevents permanent occlusion of the air bubble within the dispensed fluid, see FIGS. 4U–4W. In addition, because of the novel shape of the conduit 60, an air bubble can momentarily occlude the conduit passageway, but the novel shape of the conduit 60 prevents permanent occlusion of the conduit passageway.

The Applicant has found that fluid drops dispensed from this dropper tip 50 have been shown to be reasonably consistent in size for a given fluid. It has also been found that the presence of an occasional bubble of entrained air has been shown to have much less impact upon actual drop fluid volume than would be seen with a more traditional spherical dropper tip. Delivered drops from this structure have been found to be in the acceptable range of 25±5 microlitre size.

Attention is now directed to FIG. 5 which shows a novel closure cap 80 for sealing the dropper tip 50. Before a description of this novel closure cap 80 is provided, a description of how a prior art closure cap (not shown) would attach to the dropper tip 50 of the present invention is provided, along with the disadvantages created when a prior art closure cap is used with the novel dropper tip 50 of the present invention. Prior art closure caps provide two seals for sealing a dropper tip. When a prior art closure cap is provided on the novel dropper tip 50 of the present invention, the closure cap bears on the flat end surface 66 of the delivery tip 64 to form a first seal for preventing accumulation of liquid within the closure cap and the closure cap bears on the top of the dropper tip circular shoulder 57 to form a second seal for preventing contaminants from entering into the dropper tip 50 and to seal the dropper tip 50 to the container 52. The Applicant has found that a problem arises when such a prior art closure cap is used on the dropper tip 50 of the present invention. When the prior art closure cap is secured to the dropper tip, the cylindrical delivery tip 64 will deform as a result of the compression applied by the prior art closure cap to perfect the first seal. This causes the wall of the cylindrical delivery tip 64 to diverge outwardly and deform. This obviously is not desirable.

The novel closure cap 80 shown in FIG. 5 was developed to overcome this problem created by the prior art closure cap. The closure cap 80 is formed from a body 82 which includes a wall 84 which diverges outwardly from its first end to its second end. An end wall 86 closes the first end of the wall 84 and is angled relative to the wall 84. A circular wall 88 extends outwardly from the second end of the wall 84 and is angled relative to the wall 84. Walls 86 and 88 are parallel to each other. A depending circular skirt wall 90 extends from the outermost end of the wall 88 and is approximately perpendicular thereto. A circular shoulder 92 is formed between end wall 86 and outwardly diverging wall 84. The shoulder 92 has a curved surface 94 at its innermost point. A recess 96 is formed within the walls 84, 86, 88, 90 with one end of the recess 96 being closed by end wall 86 and the other end of the recess 96 being open. The area of the recess 96 between the shoulder 92 and end wall 86 is defined as a cap pocket. A plurality of threads 98 are provided on the interior of the wall 90 for mating with threads 57 on the container 52.

When the closure cap 80 of the present invention is secured to the container 52 and the dropper tip 50, the end wall 86 bears against the end flat 66 of the delivery tip 64. The delivery tip 64 seats within the cap pocket. The curved surface 94 bears against the curved exterior surface 100 of the body 54 proximate to the first wall portion 72. The interior of wall 88 bears against the top surface of the shoulder 59. The threads 98 are engaged with the threads 57 on the container 52.

The bearing of the curved surface 94 against the curved exterior surface 100 of the body 54 proximate to the first wall portion 72 forms the primary seal for preventing accumulation of liquid within the closure cap 80 and places the main compression load on the dropper tip 50 radius, instead of on the cylindrical delivery tip 64 as occurs with the prior art closure cap. The cylindrical delivery tip 64 of the dropper tip 50 is lightly crushed (0.002"–0.005") within the cap pocket enough to seal against the end wall 86 inner surface, but not deform the cylindrical delivery tip 64. The bearing of the interior of the wall 88 against the top surface of the shoulder 59 forms the secondary seal for preventing contaminants from entering into the dropper tip 50 and to seal the dropper tip 50 to the container 52.

While a preferred embodiment of the present invention is shown and described, it is envisioned that those skilled in the art may devise various modifications of the present invention without departing from the spirit and scope of the appended claims.

The invention claimed is:

1. A dropper tip which is adapted to be connected to a container for dispensing fluid from the container, said dropper tip comprising: a body having first and second opposite ends and an inner wall defining a conduit therethrough, said inner wall including a plurality of first wall portions and a plurality of second wall portions, each said first wall portion being radiused and being connected to at least one of said second wall portions, said inner wall smoothly transitioning from said first end to said second end such that air bubbles are prevented from being permanently trapped within said dropper tip.

2. A dropper tip as defined in claim 1, wherein each said second wall portion diverges.

3. A dropper tip as defined in claim 1, wherein said conduit increases in inner diameter from said first end to said second end.

4. A dropper tip as defined in claim 1, wherein said inner wall gradually diverges from said first end to said second end.

5. A dropper tip as defined in claim 1, wherein said body includes means for attaching said body to the container.

6. A dropper tip as defined in claim 1, wherein said first end of said body has a flat end surface to promote limited momentary attachment of fluid thereto when fluid is being dispensed from said dropper tip.

7. A dropper tip as defined in claim 6, wherein said flat end surface defines a sharp perimeter edge.

8. A dropper tip as defined in claim 1, wherein said inner wall is formed of a material which resists fluid wetting.

9. A dropper tip as defined in claim 8, wherein said inner wall is made of a fluorocarbon material.

10. A dropper tip as defined in claim 9, wherein said fluorocarbon material is selected from the group consisting of polytetrafluoroethylene, carbon tetrafluoroethylene or fluoroethylene propylene.

11. A dropper tip as defined in claim 8, wherein said inner wall is highly polished to resist fluid wetting, facilitate fluid detachment therefrom and to reduce fluid film thickness therealong.

12. A dropper tip as defined in claim 11, wherein said inner wall is made of an olefinic material.

13. A dropper tip as defined in claim 12, wherein said olefinic material is selected from the group consisting of high density polyethylene or polypropylene.

14. A dropper tip as defined in claim 13, wherein said inner wall is made of silicone rubber material.

15. A dropper tip as defined in claim 8, wherein the surface tension of the liquid is higher than the critical surface tension of the inner wall.

16. A dropper tip as defined in claim 1, wherein the surface of said inner wall is smoothed to minimize surface roughness.

17. A dropper tip which is adapted to be connected to a container for dispensing fluid from the container, said dropper tip comprising: a body having first and second opposite ends and an inner wall defining a conduit therethrough, said inner wall being formed from a first wall portion having first and second opposite ends and gradually diverging in diameter from said first end to said second end, a second wall portion having first and second opposite ends, and a third wall portion having first and second opposite ends and gradually diverging in diameter from said first end to said second end, said second end of said first wall portion smoothly transitioning with said first end of said second wall portion, and said second end of said second wall portion smoothly transitioning with said first end of said third wall portion, said first wall portion having an inner diameter at its second end which is smaller than an inner diameter of said third wall portion at its first end, said second wall portion being radiused to smoothly transition said conduit from said first wall portion to said third wall portion, said inner wall smoothly transitioning from said first end to said second end such that air bubbles are prevented from being permanently trapped within said dropper tip.

18. A dropper tip as defined in claim 17, wherein said first end of said body has a flat end surface to promote limited momentary attachment of fluid thereto when fluid is being dispensed from said dropper tip.

19. A dropper tip as defined in claim 18, wherein said flat end surface defines a sharp perimeter edge.

20. A dropper tip which is adapted to be connected to a container for dispensing fluid from the container, said dropper tip comprising: a body having first and second opposite ends and an inner wall defining a conduit therethrough, said inner wall being formed from a first wall portion having a predetermined inner dimension and first and second opposite ends, a second wall portion having first and second opposite ends, and a third wall portion having a predetermined inner dimension and first and second opposite ends, said second end of said first wall portion smoothly transitioning with said first end of said second wall portion, and said second end of said second wall portion smoothly transitioning with said first end of said third wall portion, said inner dimension of said first wall portion being smaller than said inner dimension of said third wall portion, said second wall portion being radiused to smoothly transition said conduit from said first wall portion to said third wall portion, said inner wall smoothly transitioning from said first end to said second end such that air bubbles are prevented from being permanently trapped within said dropper tip, said first wall portion gradually diverging from said first end to said second end and said third wall portion gradually diverging from said first end to said second end, the inner dimension of said first wall portion at said second end being smaller than the inner dimension of said third wall portion at its first end, and a fourth wall portion having opposite first and second ends, said second end of said fourth wall portion smoothly transitioning with said first end of said first wall portion, said fourth wall portion being radiused to smoothly transition said conduit from said first end of said body to said first end of said first wall portion.

21. A dropper tip as defined in claim 20, wherein the diameter of said fourth wall portion at its first end is smaller than at its second end.

22. A dropper tip which is adapted to be connected to a container for dispensing fluid from the container, said dropper tip comprising: a body having first and second opposite ends and an inner wall defining a conduit therethrough, said inner wall is formed of a material which resists fluid wetting and which has a critical surface tension equal to or less than 31 dynes/cm, and said inner wall smoothly transitioning from said first end to said second end such that air bubbles are prevented from being permanently trapped along said inner wall, said inner wall being formed from a first wall portion having a predetermined inner dimension and first and second opposite ends, a second wall portion having first and second opposite ends, and a third wall portion having a predetermined inner dimension and first and second opposite ends said second end of said first wall portion smoothly transitioning with said first end of said second wall portion, and said second end of said second wall portion smoothly transitioning with said first end of said third wall portion, said inner dimension of said first wall portion being smaller than said inner dimension of said third wall portion, said second wall portion being radiused to smoothly transition said conduit from said first wall portion to said third wall portion, said inner wall smoothly transitioning from said first end to said second end such that air bubbles are prevented from being permanently trapped within said dropper tip, said first wall portion gradually diverging from said first end to said second end and said third wall portion gradually diverging from said first end to said second end, the diameter of said first wall portion said second end being smaller than the diameter of said third wall portion at its first end.

23. A dropper tip as defined in claim 22, wherein said inner wall is made of a fluorocarbon material.

24. A dropper tip as defined in claim 23, wherein said fluorocarbon material is selected from the group consisting of polytetrafluoroethylene, carbon tetrafluoroethylene or fluoroethylene propylene.

25. A dropper tip as defined in claim 22, wherein said inner wall is highly polished to resist fluid wetting, facilitate fluid detachment therefrom and to reduce fluid film thickness therealong.

26. A dropper tip as defined in claim 25, wherein said inner wall is made of an olefinic material.

27. A dropper tip as defined in claim 26, wherein said olefinic material is selected from the group consisting of high density polyethylene or polypropylene.

28. A dropper tip as defined in claim 25, wherein said inner wall is made of silicone rubber material.

29. A dropper tip as defined in claim 22, wherein the surface of said inner wall is smoothed to minimize surface roughness.

30. A dropper tip as defined in claim 22, wherein said inner wall gradually diverges from said first end to said second end.

31. A dropper tip as defined in claim 22, wherein the surface tension of the liquid is higher than the critical surface tension of the inner wall.

32. A dropper tip as defined in claim 22, wherein said first end of said body has a flat end surface to promote limited momentary attachment of fluid thereto when fluid is being dispensed from said dropper tip.

33. A dropper tip as defined in claim 32, wherein said flat end surface defines a sharp perimeter edge.

34. A dropper tip which is adapted to be connected to a container for dispensing fluid from the container, said dropper tip comprising: a body having first and second opposite ends and an inner wall defining a conduit therethrough, said inner wall is formed of a material which resists fluid wetting, and said inner wall smoothly transitioning from said first end to said second end such that air bubbles are prevented from being permanently trapped along said inner wall, said inner wall being formed from a first wall portion having a predetermined inner dimension and first and second opposite ends, a second wall portion having first and second opposite ends, and a third wall portion having a predetermined inner dimension and first and second opposite ends, said second end of said first wall portion smoothly transitioning with said first end of said second wall portion, said second end of said second wall portion smoothly transitioning with said first end of said third wall portion, said inner dimension of said first wall portion being smaller than said inner dimension of said third wall portion, said second wall portion being radiused to smoothly transition said conduit from said first wall portion to said third wall portion, said inner wall smoothly transitioning from said first end to said second end such that air bubbles are prevented from being permanently trapped within said dropper tip, and said first wall portion gradually diverging from said first end to said second end and said third wall portion gradually diverging from said first end to said second end, the dimension of said first wall portion at said second end being smaller than the dimension of said third wall portion at its first end, and a fourth wall portion having opposite first and second ends, said second end of said fourth wall portion smoothly transitioning with said first end of said first wall portion, said fourth wall portion being radiused to smoothly transition said conduit from said first end of said body to said first end of said first wall portion.

35. A dropper tip as defined in claim 34, wherein the diameter of said fourth wall portion at its first end is smaller than at its second end.

36. A dropper tip which is adapted to be connected to a container for dispensing fluid from the container, said dropper tip comprising: a body having first and second opposite ends and an inner wall defining a conduit therethrough for the passage of fluid therethrough, said first end of said body having a flat end surface to promote limited momentary attachment of fluid thereto when fluid is being dispensed from said dropper tip, said inner wall being formed from a first wall portion having a predetermined inner dimension and first and second opposite ends, a second wall portion having first and second opposite ends, a third wall portion having a predetermined inner dimension and first and second opposite ends, said second end of said first wall portion smoothly transitioning with said first end of said second wall portion, and said second end of said second wall portion smoothly transitioning with said first end of said third wall portion, said inner dimension of said first wall portion being smaller than said inner dimension of said third wall portion, said second wall portion being radiused to smoothly transition said conduit from said first wall portion to said third wall portion, said first wall portion gradually diverges from said first end to said second end and said third wall portion gradually diverges from said first end to said second end, the dimension of said first wall portion at said second end being smaller than the dimension of said third wall portion at its first end, and a fourth wall portion having opposite first and second ends, said second end of said fourth wall portion smoothly transitioning with said first end of said first wall portion, said fourth wall portion being radiused to smoothly transition said conduit from said first end of said body to said first end of said first wall portion.

37. A dropper tip as defined in claim 36, wherein the diameter of said fourth wall portion at its first end is smaller than at its second end.

38. In combination, a dropper tip, a container and a cap, comprising: said dropper tip comprising a body having first and second opposite ends and an inner wall defining a conduit therethrough, said inner wall including a plurality of first wall portions and a plurality of second wall portions, each said first wall portion being radiused and being connected to at least one of said second wall portions, said inner wall smoothly transitioning from said first end to said second end such that air bubbles are prevented from being permanently trapped within said dropper tip, said dropper tip being engaged with said container; said container comprising a body; and said cap comprising a body having first sealing means for bearing against one of said first wall portions of said dropper tip to seal said first end of said dropper tip.

39. The combination as defined in claim 38, wherein said dropper tip includes a cylindrical projection on an end thereof and one of said first wall portions is connected to said cylindrical projection, said cylindrical projection being seated within a recess provided in said cap when said cap is mated with said container, said first sealing means bearing against said dropper tip proximate to said cylindrical projection.

40. The combination as defined in claim 38, wherein said dropper tip further includes a circular flange projecting outwardly from said body at a predetermined distance from said second end, said body of said cap further having second sealing means for bearing against said flange to seal said dropper tip.

41. The combination as defined in claim 38, wherein said body of said container has means thereon for engaging said cap, and said body of said cap having means for engaging said means on said container.

* * * * *